(12) United States Patent
Mensing et al.

(10) Patent No.: US 12,349,788 B2
(45) Date of Patent: Jul. 8, 2025

(54) CONFIGURATION TECHNIQUES FOR AN APPLIANCE WITH CHANGEABLE COMPONENTS

(71) Applicant: Ergotron, Inc., St. Paul, MN (US)

(72) Inventors: Jeffrey Randall Mensing, Eden Prairie, MN (US); Jeffrey Aymond, Inver Grove Heights, MN (US); Nicholas Simon Hazzard, Oakdale, MN (US)

(73) Assignee: Ergotron, Inc., St. Paul, MN (US)

( * ) Notice: Subject to any disclaimer, the term of this patent is extended or adjusted under 35 U.S.C. 154(b) by 176 days.

(21) Appl. No.: 18/155,476

(22) Filed: Jan. 17, 2023

(65) Prior Publication Data

US 2023/0172353 A1    Jun. 8, 2023

Related U.S. Application Data

(63) Continuation of application No. 17/288,192, filed as application No. PCT/US2020/054696 on Oct. 8, 2020, now Pat. No. 11,607,038.
(Continued)

(51) Int. Cl.
*A61B 50/13* (2016.01)
*A47B 67/02* (2006.01)
(Continued)

(52) U.S. Cl.
CPC .............. *A47B 67/02* (2013.01); *A61B 50/13* (2016.02); *A61B 50/18* (2016.02);
(Continued)

(58) Field of Classification Search
CPC ......... A47B 67/02; A61B 50/13; A61B 50/18; A61B 2050/105; A61B 2050/185
(Continued)

(56) References Cited

U.S. PATENT DOCUMENTS 4,833,605 A   5/1989   Terada et al.
4,847,764 A   7/1989   Halvorson
(Continued)

FOREIGN PATENT DOCUMENTS

CA    2138215 A1    8/1995
CN    103417347    * 12/2013    ............. A61G 12/00
(Continued)

OTHER PUBLICATIONS

"U.S. Appl. No. 17/288,192 Preliminary Amendment Filed with Application Apr. 23, 2021", 8 pgs.
(Continued)

*Primary Examiner* — James O Hansen
(74) *Attorney, Agent, or Firm* — Schwegman Lundberg & Woessner, P.A.

(57) ABSTRACT

The present disclosure relates to a workstation and a technique to automatically configure the workstation. The workstation can be used to perform various tasks including but not limited to medication delivery, collection of medical records, patient care, manufacturing operations, and others. The workstation can be configured by the user depending on the tasks to be performed using the workstation. Various sensors (e.g., hall effect sensors, optical sensors, or the like) can be coupled to the workstation, and sensor operators (e.g., magnets, color coded strips, or the like) can be coupled to the modules. By aligning sensor operators with sensors when modules are coupled to the workstation, a configuration (e.g., size, shape, location, or the like) of modules can be automatically detected by the workstation controller. The controller of the workstation can then adapt to perform certain tasks (e.g., lock/unlock drawers, or the like) depending on the detected configuration of modules.

20 Claims, 25 Drawing Sheets

Related U.S. Application Data

(60) Provisional application No. 62/914,216, filed on Oct. 11, 2019.

(51) Int. Cl.
  *A61B 50/18* (2016.01)
  *A61B 50/10* (2016.01)

(52) U.S. Cl.
  CPC ... *A47B 2067/025* (2013.01); *A61B 2050/105* (2016.02); *A61B 2050/185* (2016.02)

(58) Field of Classification Search
  USPC .................................. 312/209, 249.8, 249.11
  See application file for complete search history.

(56) References Cited

U.S. PATENT DOCUMENTS

| | | | |
|---|---|---|---|
| 5,314,243 | A | 5/1994 | Mcdonald et al. |
| 5,347,267 | A | 9/1994 | Murray |
| 5,359,322 | A | 10/1994 | Murray |
| 5,564,803 | A | 10/1996 | Mcdonald et al. |
| 5,905,653 | A | 5/1999 | Higham et al. |
| 6,175,779 | B1 | 1/2001 | Barrett |
| 6,470,234 | B1 | 10/2002 | Mcgrady |
| 6,564,121 | B1 | 5/2003 | Wallace et al. |
| 6,629,172 | B1 | 9/2003 | Andersson et al. |
| 6,738,920 | B1 | 5/2004 | Horne |
| 7,152,441 | B2 | 12/2006 | Friar et al. |
| 7,719,420 | B2 | 5/2010 | Christie et al. |
| 8,085,128 | B2 | 12/2011 | Colley, III |
| 8,109,527 | B2 * | 2/2012 | Bustle .................. A61G 12/001 280/47.35 |
| 8,126,590 | B2 | 2/2012 | Vahlberg et al. |
| 8,179,228 | B2 | 5/2012 | Colley, III et al. |
| 8,180,485 | B2 | 5/2012 | Reckelhoff |
| 8,210,548 | B1 | 7/2012 | Agyemang |
| 8,280,550 | B2 | 10/2012 | Levy et al. |
| 8,631,179 | B1 | 1/2014 | Faulds |
| 8,812,153 | B2 | 8/2014 | Reckelhoff |
| 8,818,552 | B2 | 8/2014 | Heffron |
| 8,914,148 | B2 | 12/2014 | Wagner |
| 9,135,482 | B2 | 9/2015 | Caputo et al. |
| 9,155,682 | B2 | 10/2015 | Boyd |
| 9,157,261 | B2 | 10/2015 | Rahilly |
| 9,158,892 | B2 | 10/2015 | Levy et al. |
| 9,298,887 | B2 | 3/2016 | Clark et al. |
| 9,355,218 | B2 | 5/2016 | Brown et al. |
| 9,355,219 | B2 | 5/2016 | Paydar et al. |
| 9,367,984 | B2 | 6/2016 | Daugbjerg et al. |
| 9,569,592 | B2 | 2/2017 | Heffron |
| 9,579,245 | B2 | 2/2017 | Larkner et al. |
| 9,587,878 | B2 | 3/2017 | Paydar et al. |
| 9,652,594 | B2 | 5/2017 | Olson et al. |
| 9,715,671 | B2 | 7/2017 | Vahlberg et al. |
| 9,747,743 | B2 | 8/2017 | Brown |
| 9,977,873 | B1 | 5/2018 | Shoenfeld |
| 10,045,899 | B2 | 8/2018 | Sciacchitano et al. |
| 10,045,900 | B2 | 8/2018 | Sciacchitano et al. |
| 10,453,572 | B1 * | 10/2019 | Brooks .................. G16H 40/40 |
| 11,607,038 | B2 | 3/2023 | Mensing et al. |
| 2002/0035658 | A1 | 3/2002 | Whetsel |
| 2002/0188781 | A1 | 12/2002 | Schoch et al. |
| 2003/0126356 | A1 | 7/2003 | Gustavson et al. |
| 2004/0133705 | A1 | 7/2004 | Broussard et al. |
| 2006/0125356 | A1 | 6/2006 | Meek et al. |
| 2007/0055116 | A1 | 3/2007 | Clark et al. |
| 2007/0227409 | A1 * | 10/2007 | Chu ........................ A47B 21/00 108/50.02 |
| 2008/0004908 | A1 | 1/2008 | Oh et al. |
| 2008/0059191 | A1 | 3/2008 | Huang et al. |
| 2008/0140916 | A1 | 6/2008 | Oh et al. |
| 2009/0133609 | A1 | 5/2009 | Nethken et al. |
| 2009/0212670 | A1 * | 8/2009 | Bustle .................. A61G 12/001 312/333 |
| 2010/0134243 | A1 | 6/2010 | Colley, III et al. |
| 2012/0274196 | A1 * | 11/2012 | Arceta .................. B62B 3/1476 312/249.11 |
| 2013/0018505 | A1 | 1/2013 | Barrett et al. |
| 2013/0057339 | A1 | 3/2013 | Koudar |
| 2013/0200586 | A1 * | 8/2013 | Trish .................... A61G 12/001 280/79.3 |
| 2013/0246198 | A1 | 9/2013 | Truong et al. |
| 2013/0322002 | A1 | 12/2013 | Clark et al. |
| 2014/0001930 | A1 | 1/2014 | Slogoff et al. |
| 2014/0163726 | A1 | 6/2014 | Shoenfeld et al. |
| 2014/0184038 | A1 | 7/2014 | Shoenfeld |
| 2014/0246964 | A1 | 9/2014 | Boyd |
| 2015/0148946 | A1 | 5/2015 | Barrett et al. |
| 2015/0196445 | A1 | 7/2015 | Larkner et al. |
| 2016/0095779 | A1 | 4/2016 | Canady et al. |
| 2016/0294947 | A1 | 10/2016 | Abu-Tarif et al. |
| 2017/0109480 | A1 | 4/2017 | Vahlberg |
| 2017/0172412 | A1 | 6/2017 | Abu-Tarif et al. |
| 2017/0258658 | A1 | 9/2017 | Larkner et al. |
| 2018/0008497 | A1 * | 1/2018 | Sciacchitano ....... E05B 47/0001 |
| 2018/0256427 | A1 | 9/2018 | Volek et al. |
| 2018/0325762 | A1 | 11/2018 | Hazzard |
| 2019/0270471 | A1 * | 9/2019 | Hazzard ................ H02J 7/0045 |
| 2022/0225764 | A1 | 7/2022 | Mensing et al. |

FOREIGN PATENT DOCUMENTS

| | | |
|---|---|---|
| CN | 107111678 A | 8/2017 |
| CN | 114630600 A | 6/2022 |
| WO | WO-2006056002 A1 | 6/2006 |
| WO | WO-2013056025 A1 | 4/2013 |
| WO | WO-2016085708 A2 | 6/2016 |
| WO | WO-2016085708 A3 | 6/2016 |
| WO | WO-2021072018 A1 | 4/2021 |

OTHER PUBLICATIONS

"U.S. Appl. No. 17/288,192, Notice of Allowance mailed Nov. 16, 2022", 11 pgs.

"U.S. Appl. No. 17/288,192, Response filed Sep. 2, 2022 to Restriction Requirement mailed Jul. 6, 2022", 7 pgs.

"U.S. Appl. No. 17/288,192, Restriction Requirement mailed Jul. 6, 2022".

"International Application Serial No. PCT/US2020/054696, International Preliminary Report on Patentability mailed Apr. 21, 2022", 8 pgs.

"International Application Serial No. PCT/US2020/054696, International Search Report mailed Jan. 28, 2021", 2 pgs.

"International Application Serial No. PCT/US2020/054696, Written Opinion mailed Jan. 28, 2021", 6 pgs.

"Style View(r) SV43 Cart with LCD Arm", User Guide, Ergotron(r), (2014), 16 pgs.

"Style View(r) SV43/44 Supplemental Drawer", User Guide, Ergotron(r), (2014), 8 pgs.

"Canadian Application Serial No. 3,154,408, Office Action mailed Aug. 5, 2024", 3 pgs.

"Canadian Application Serial No. 3, 154,408, Office Action mailed Sep. 1, 2023", 3 pgs.

"Canadian Application Serial No. 3,154,408, Response filed Dec. 28, 2023 to Office Action mailed Sep. 1, 2023", w/ claims, 20 pgs.

"Chinese Application Serial No. 202080071235.3, Office Action mailed Jul. 9, 2024", W/English Translation, 7 pgs.

"Chinese Application Serial No. 202080071235.3, Office Action mailed Oct. 24, 2023", 18 pgs.

"Chinese Application Serial No. 202080071235.3, Response filed Apr. 30, 2024 to Office Action mailed Oct. 24, 2023", w/ English Claims, 11 pgs.

"Chinese Application Serial No. 202080071235.3, Response filed Aug. 15, 2024 to Office Action mailed Jul. 9, 2024", w/ english claims, 10 pgs.

"Chinese Application Serial No. 202080071235.3, Voluntary Amendment filed Feb. 1, 2023, w/ English Claims, 9 pgs.

(56) References Cited

OTHER PUBLICATIONS

"European Application Serial No. 20874190.0, Extended European Search Report mailed Oct. 23, 2023", 8 pgs.

"European Application Serial No. 20874190.0, Response filed May 6, 2024 to Extended European Search Report mailed Oct. 23, 2023", 13 pgs.

"European Application Serial No. 20874190.0, Response filed Nov. 21, 2022 to Communication pursuant to Rules 161(2) and 162 EPC", 8 pgs.

* cited by examiner

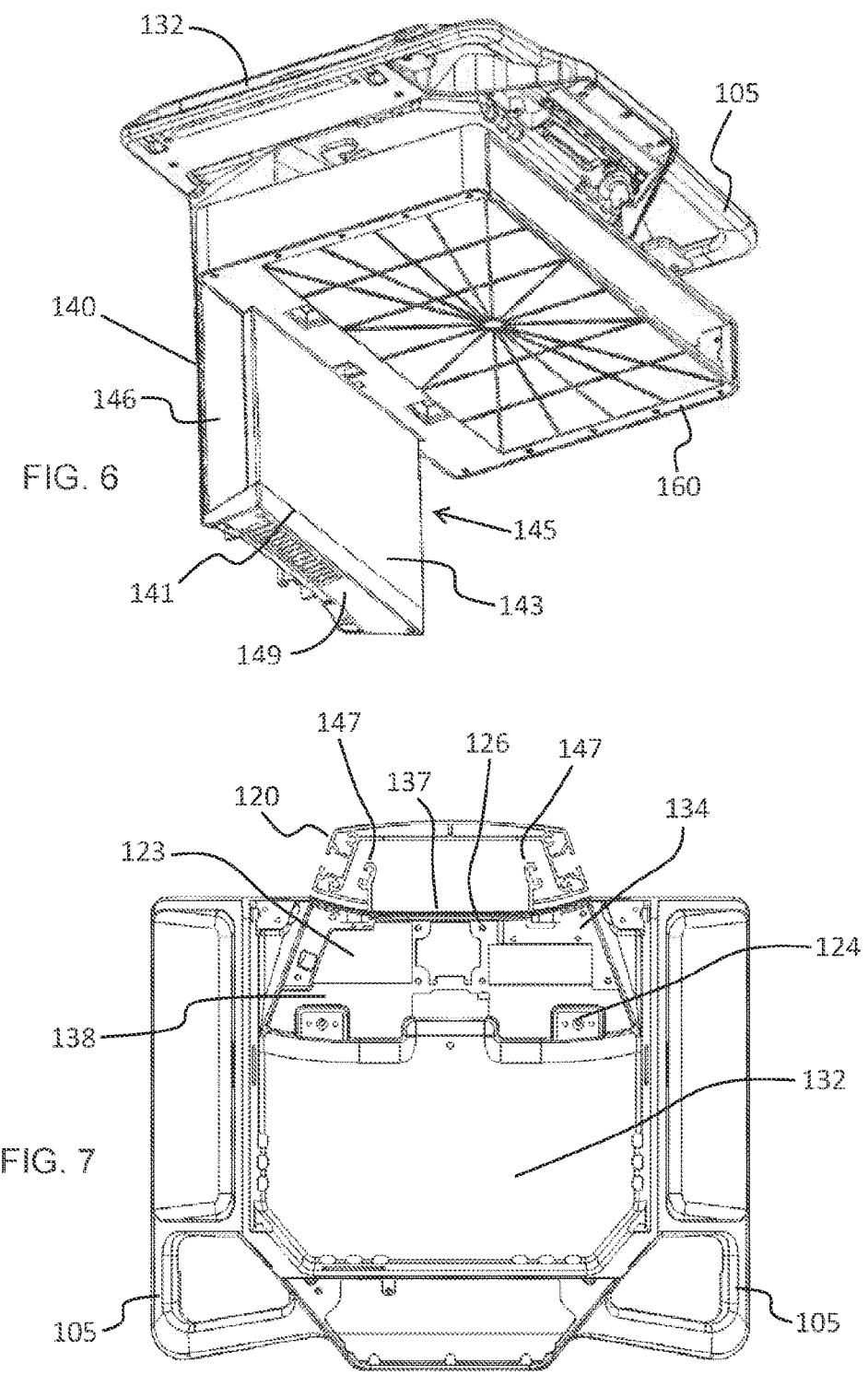

CONFIGURATION TECHNIQUES FOR AN APPLIANCE WITH CHANGEABLE COMPONENTS

CLAIM OF PRIORITY

This patent application is a continuation of U.S. application Ser. No. 17/288,192, entitled "CONFIGURATION TECHNIQUES FOR AN APPLIANCE WITH CHANGEABLE COMPONENTS," filed Apr. 23, 2021, now U.S. Pat. No. 11,607,038, which is a U.S. NSPCT Application claiming the benefit of priority to PCT Application Serial No. PCT/US2020/054696, entitled "CONFIGURATION TECHNIQUES FOR AN APPLIANCE WITH CHANGEABLE COMPONENTS," filed Oct. 8, 2020, and published as WO 2021/072018 A1 on Apr. 15, 2021, which claims the benefit of priority of Ergun, et al. U.S. Provisional Patent Application Ser. No. 62/914,216, entitled "CONFIGURATION TECHNIQUES FOR AN APPLIANCE WITH CHANGEABLE COMPONENTS," filed on Oct. 11, 2019, which is hereby incorporated by reference herein in their entirety.

TECHNICAL FIELD

This document pertains generally, but not by way of limitation, to modular construction and operation of appliances.

BACKGROUND

Appliances can be freestanding (e.g., cabinets supported by a floor or a desk), coupled to a structure (e.g., cabinets coupled to a wall), or mobile (e.g., workstations coupled to a wheeled base). Appliances can be used to accomplish one or more tasks (e.g., medication delivery, collection of electronic medical records, patient care, manufacturing operations, or the like). Various external components (e.g., drawers, bins, batteries, scanners, wipes containers, computers, or the like) can be coupled to the appliance depending on the task they will perform.

BRIEF DESCRIPTION OF THE DRAWINGS

The following drawings are illustrative of particular non-limiting example configurations of the present invention and therefore do not limit the scope of the invention. The drawings are not to scale and are intended for use in conjunction with the explanations in the following detailed description. Example configurations of the present invention will hereinafter be described in conjunction with the appended drawings. The drawings illustrate generally, by way of example, but not by way of limitation, various configurations discussed in the present document.

FIG. 6 illustrates a bottom perspective view of the sub-assembly of FIG. 5, according to an example configuration of the present disclosure.

FIG. 7 illustrates a top view of the sub-assembly of FIG. 5, according to an example configuration of the present disclosure.

OVERVIEW

This disclosure relates to an appliance and a method to automatically detect a configuration of the appliance. The appliance can be in various shapes and forms including, but not limited to, a workstation, a furniture, a cabinet, a computing cart, a charging station, or the like. The appliance can be used to perform various tasks including, but not limited to, medication delivery, collection of electronic medical records, patient care, manufacturing operations, and others. The appliance can be configured and reconfigured by adding or removing components depending on the task to be performed by the appliance. These changeable components (e.g., modules) can include, but not limited to, drawers, bins, document holders, batteries, computers, and others. Various sensors (e.g., an optical sensors, a hall effect sensor, a potentiometer, an accelerometer, a proximity sensor, a pressure sensor, a temperature sensor, an IR sensor, a motion detector, a force sensor, a contact sensor, a current sensor, or the like) can be coupled to the appliance, and matching sensor operators (e.g., magnets, color coded strips, or the like) can be coupled to the modules. Sensor operators can be uniquely arranged to represent various types and configurations of modules (e.g., different size and location of drawers, or the like). By aligning sensor operators with sensors when modules are coupled to the appliance, type, configuration, and location of various modules can be automatically detected by the controller of the appliance. The controller of the appliance can then adapt to perform certain tasks (e.g., lock/unlock different size and shape drawers, or the like) depending on the detected configuration of modules.

DETAILED DESCRIPTION

The following detailed description is illustrative in nature and is not intended to limit the scope, applicability, or configuration of the invention in any way. Rather, the following description provides some practical illustrations for implementing various configurations of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

This disclosure describes the construction of an appliance (e.g., a cabinet 40, a mobile workstation 100, or the like) in FIGS. 1-12 according to some example configurations of the current disclosure.

Figure 1A:
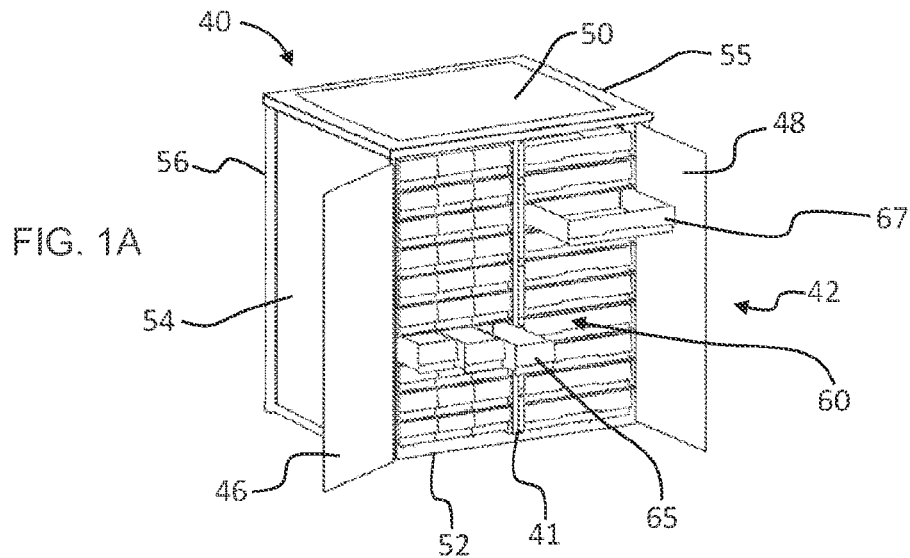
FIG. 1A illustrates a perspective view of a cabinet with changeable drawers, according to an example configuration of the present subject matter.
Figure 1B:
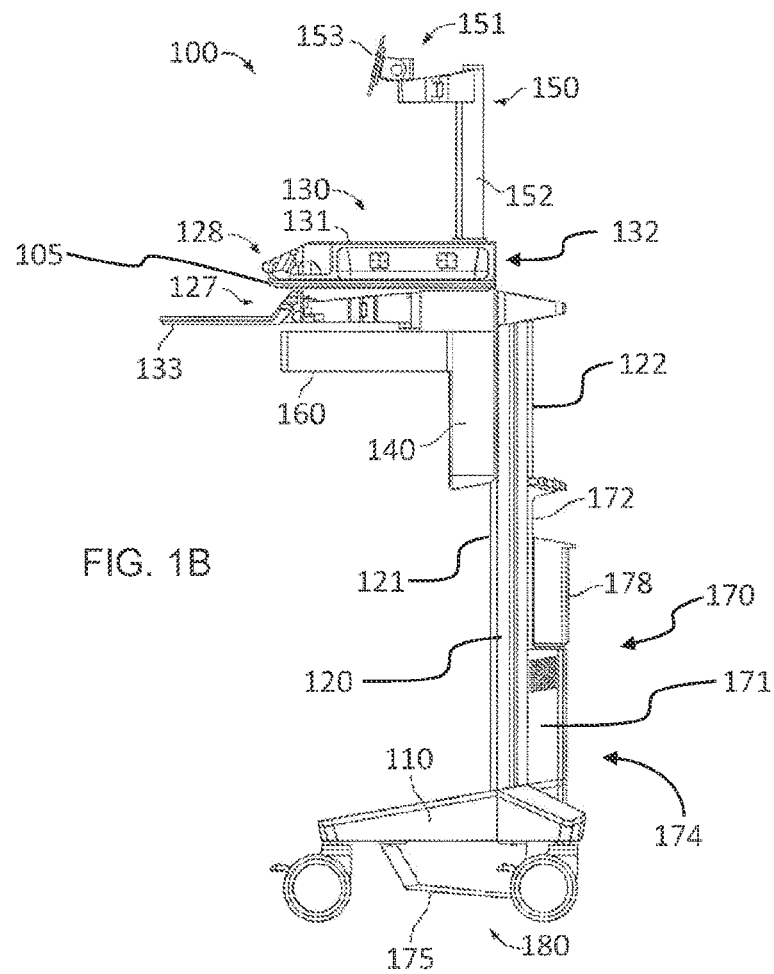
FIG. 1B illustrates a side view of a mobile workstation, according to an example configuration of the present disclosure.

The appliance (e.g., the cabinet 40 of FIG. 1A, the workstation 100 of FIG. 1B, or the like) can include one or more modules (e.g., drawer housings 60 of FIG. 1A, or drawer housings 160 of FIG. 1B, or the like). This disclosure describes the construction and coupling of one or more drawer housings 160 to the workstation 100 in FIGS. 13-20 according to some example configurations of the current disclosure.

One or more drawers can be contained inside the one or more drawer housings 160. Various drawer configurations are described in FIGS. 36-41.

Figure 42:
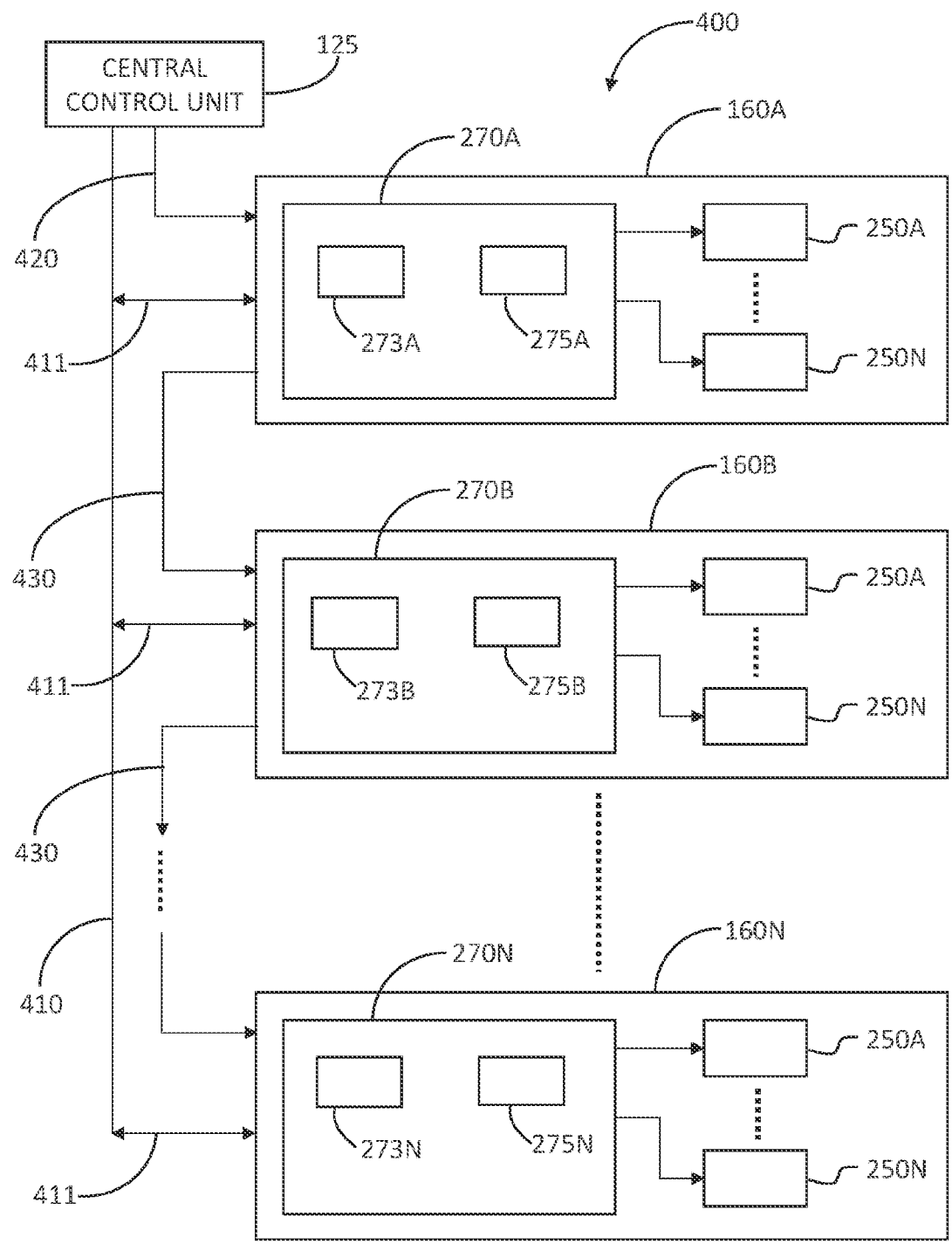
FIG. 42 illustrates a block diagram representation of the dynamic addressing method, according to an example configuration of the present disclosure.
Figure 43A:
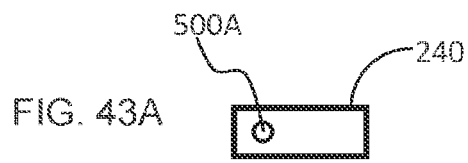
FIG. 43A illustrates a block diagram of a single-stall drawer with a magnet, according to an example configuration of the present disclosure.
Figure 43B:
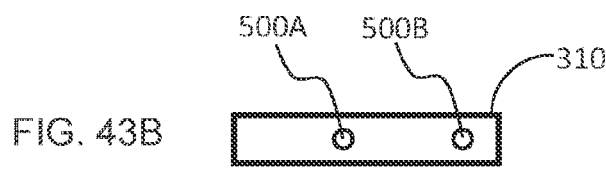
FIG. 43B illustrates a block diagram of a dual-stall drawer with magnets, according to an example configuration of the present disclosure.
Figure 43C:
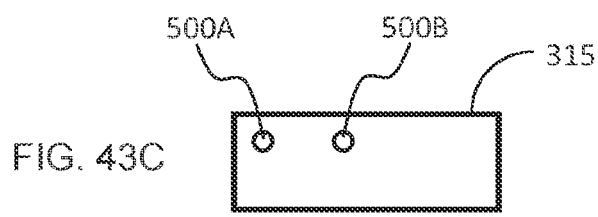
FIG. 43C illustrates a block diagram of a dual stall/tall drawer with magnets, according to an example configuration of the present disclosure.
Figure 43D:
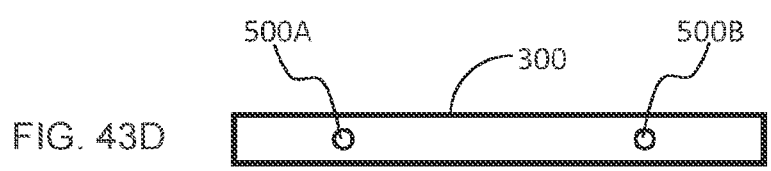
FIG. 43D illustrates a block diagram of a quad stall drawer with magnets, according to an example configuration of the present disclosure.
Figure 43E:
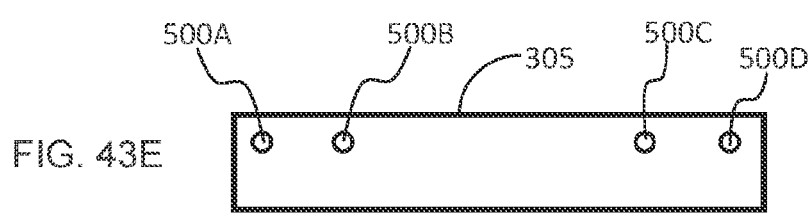
FIG. 43E illustrates a block diagram of a quad stall/tall drawer with magnets, according to an example configuration of the present disclosure.

Operation and control of the drawers according to dynamic addressing method is described in FIG. 42.

The drawer housing can further include a lock assembly 220. This disclosure describes the construction and operation of the lock assembly 220 in FIGS. 22-31.

This disclosure also describes various techniques to automatically determine a configuration (e.g., size, location, or the like) of the drawers in FIGS. 32-35 and in FIGS. 43-45.

FIG. 1A shows a perspective view of a cabinet 40. The cabinet 40 can include a frame 41. An upper surface 50 and a lower surface 52 opposite the upper surface 50 can be coupled to the frame 41. The cabinet 40 can further include a left-side wall 54, a right-side wall 55 and a rear wall 56.

A left door 46 and a right door 48 can be built into the front side 42 of the cabinet. The upper surface 50, the lower surface 52, the left-side wall 54, the right-side wall 55, the rear wall 56, and left door 46 and the right door 48 can form an enclosure of the cabinet 40. The left door 46 and the right door 48 can be in an open configuration or in a closed configuration. In the open configuration of the left 46 and right 48 doors as illustrated in FIG. 1A, various modules (e.g., drawer housings 60, or the like) can be inserted into the enclosure of the cabinet 40. In the closed configuration (not shown), modules can be securely contained in the enclosure of the cabinet 40. In some example configurations, a lock (not shown in FIG. 1A) can be coupled to the left door 46 and the right door 48 to prevent them from opening. In some example configurations, the one or more drawers in various sizes and shapes (e.g., a small drawer 65, a large drawer 67, or the like) can be inserted into the drawer housing 60.

FIG. 1B shows a side view of an example of a mobile workstation 100. The mobile workstation 100 can include a wheeled base 110, and a support structure 120 (e.g., a fixed-height riser, or a telescoping riser, or the like) can be coupled to the wheeled base 110. A moving bracket (not shown in FIG. 1B) can be slidably engaged with the support structure 120. A head unit assembly 130 and a cable storage box 140 can be coupled to the moving bracket n some example configurations. The cable storage box 140 can retain one or more cables and power connectors (e.g., a power outlet strip). In some example configurations, the mobile workstation 100 can include a handle 105 to facilitate transportation of the workstation 100.

A counterbalance mechanism 115 (shown in FIG. 2) can be coupled to the support structure 120 and can be coupled to the moving bracket. As described herein, the counterbalance mechanism 115 can provide height adjustment for the moving bracket. The distance between the wheeled base 110, and the head unit assembly 130 can be selectively adjusted by translating the moving bracket with respect to the wheeled base along a portion of the support structure 120.

The head unit assembly 130 can include a worksurface 131 and a computer storage compartment 132. For instance, the computer storage compartment 132 can be located beneath the worksurface 131. Additionally, a keyboard tray 133 can be located below the computer storage compartment 132. A keyboard tray arm assembly 127 can be coupled to the head unit assembly 130, and to the keyboard tray 133. The keyboard tray arm assembly 127 can provide some articulation for the keyboard tray 133 relative to the worksurface 131.

In some example configurations, the mobile workstation 100 of FIG. 1B can further include a drawer housing 160. The one or more drawers can be located inside the drawer housing to store items, e.g., medicine or other medical equipment. In some configurations, the one or more drawers can be locked inside the drawer housing 160 to secure various items contained inside the one or more drawers.

A display mount assembly 150 can be coupled to the mobile workstation 100. For instance, the display mount assembly 150 can be located above the worksurface 131. The display mount assembly 150 can include a display mount 153, a display arm assembly 151 and a display mounting riser 152. The display mounting riser 152 can be coupled to the head unit 130. The display arm assembly 151 can be coupled to the display mounting riser 152 and to the display mount 153. The display arm assembly 151 can provide some articulation for the display mount 153 relative to the display mounting riser 152. A display (not shown in FIG. 1B) can be coupled to the display mount 153 to position the display above the worksurface 131. In some examples, the display mounting riser 152 can provide height adjustment for the display relative to the worksurface 131.

The mobile workstation 100 of FIG. 1B can further include a power system 170. The power system 170 of the mobile workstation 100 can include a resident battery 180, e.g., located inside a housing 175 coupled to the base 110. A power module housing 171 and a battery connection housing 172 can be coupled to a rear side of the support structure 120. A power module 174 can be located inside the power module housing 171, e.g., inside a vertical portion of the power module housing 171. A replaceable battery 178 can be removably coupled to the battery connection housing 172.

The power module 174 can include an AC/DC power supply, an inverter, a battery charging circuit, and a controller (none of which are shown in FIG. 1B), such as shown in commonly assigned U.S. patent application Ser. No. 16/290,831 to Hazzard et al. and titled "POWER SYSTEM FOR MOBILE WORKSTATION," filed on Mar. 1, 2019 and herein incorporated by reference in its entirety. The controller can be in electrical communication with the resident battery 180 and replaceable battery 178 to provide electrical power for the electronic components (e.g., computer, display, among other things) coupled to the mobile workstation 100 according to a pre-defined logic.

Figure 2:
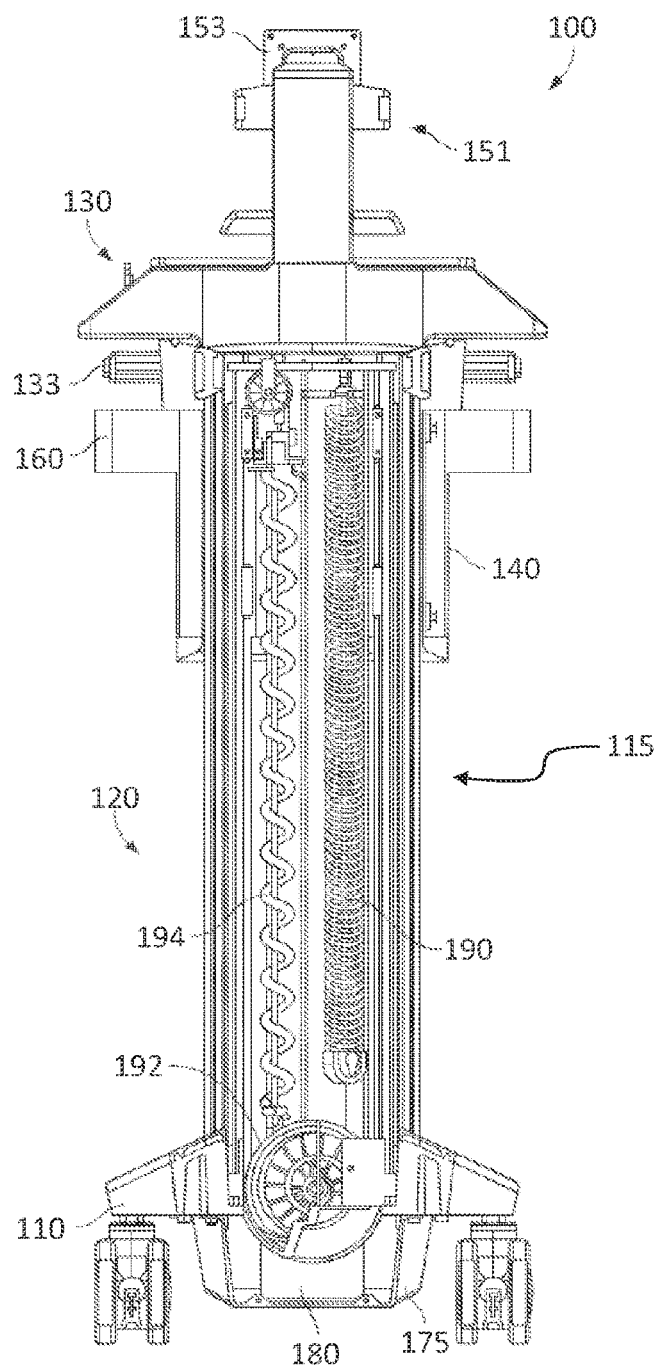
FIG. 2 illustrates a rear cutaway view of the mobile workstation of FIG. 1B, according to an example configuration of the present disclosure.

FIG. 2 is a partial rear cutaway view of the mobile workstation 100 of FIG. 1B. As seen in FIG. 2, the support structure 120 can include a counterbalance mechanism 115 having a spring 190 (e.g., an extension spring, or compression spring), and a cam/wheel assembly 192. The counterbalance mechanism 115 can be operatively coupled to the support structure 120 and to the moving bracket (not shown in FIG. 2), and can provide a counterbalance lift force for at least a portion of the total weight of various components coupled to the head unit assembly 130 (e.g., head unit assembly 130, display mounting assembly 150, display, keyboard, drawer housing 160, drawers and their content, other medical equipment located on the worksurface 131, and the like) throughout the height adjustment.

In the example shown in FIG. 2, a coiled power cord 194 can be located inside the support structure 120. One end of the coiled power cord 194 can be coupled to the power module 174 and the other end of the coiled power cord 194 can be coupled to an outlet strip, e.g., located inside the head unit assembly 130. The coiled power cord 194 can expand and contract during the height adjustment of the head unit 130 and can provide power to various electronic devices electrically coupled to the head unit assembly 130, e.g., computing devices and electronic displays.

Figure 3:
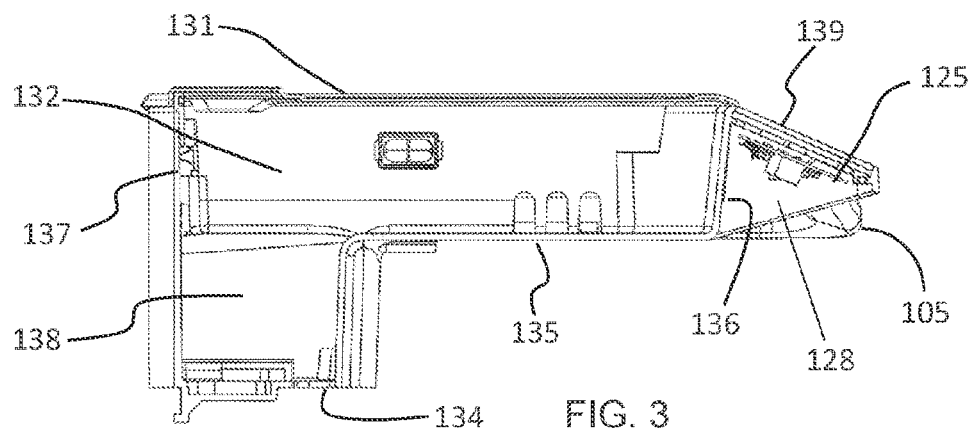
FIG. 3 illustrates a side cutaway view of the computer storage compartment of the mobile workstation of FIG. 1B, according to an example configuration of the present disclosure

FIG. 3 is a side view of the computer storage compartment 132 of the mobile workstation 100 of FIG. 1B. The computer storage compartment 132 can be an enclosed space to store and secure electronic components including (but not limited to) a computer, one or more cables, a charger, a power brick, and others. The computer storage compartment 132 can include a lower surface 135, a front wall 136, a rear wall 137, and a right and a left side walls connecting the front 136 and rear 137 walls. The front wall, the rear wall, the right-side wall, and the left-side wall extend from the lower surface 135 in transverse direction. The worksurface 131 can be removably coupled to the upper end of the computer storage compartment 132. In some example configurations, the computer storage compartment 132 can include a lock (not shown in FIG. 3). The lock can selectively engage with or disengage from the worksurface 131. When it is engaged, the lock can prevent the worksurface 131 to be removed from the computer storage compartment 132.

In some example configurations, the lower surface 135 of the computer storage compartment 132 can include a recessed section 138 proximate the rear wall 137. The lower end of the recessed section 138 can include a bottom surface 134. The bottom surface 134 can include one or more features to couple the computer storage compartment 132 to the mobile workstation 100 as discussed below in this disclosure.

The bottom surface 134 can include an opening 123. The opening 123 can align with the cable storage box 140, and it can provide a cable routing channel between the cables stored inside the cable storage box 140 and various electronic equipment located inside the computer storage compartment 132. The bottom surface 134 can further include one or more recesses 124 as illustrated in FIG. 7. The one or more recesses 124 can align with one or more connectors (e.g., a first mechanical connector 222 and a second mechanical connector 224 of FIG. 16A) located on the drawer housing 160 when the drawer housing 160 is coupled to the workstation 100.

Figure 4:
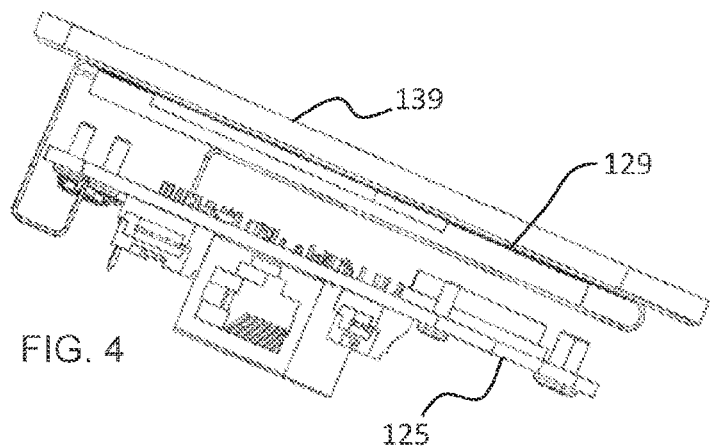
FIG. 4 illustrates the central control unit of the mobile workstation of FIG. 1B, according to an example configuration of the present disclosure.

A control unit housing 128 can be coupled to the front wall 136 of the computer storage compartment 132. In some example configurations, the control unit housing 128 can be formed as an integral part of the computer storage compartment 132. A central control unit 125 can be located inside the control unit housing 128 as shown in FIGS. 3-4 according to an example configuration of the current disclosure. The central control unit 125 can perform various workstation functions including (but not limited to) work surface height adjustment, battery monitoring, drawer control, and others.

The control unit housing 128 can have an upper surface 139. A touch sensitive LCD screen 129 can be located beneath the upper surface 139. The upper surface 139 can be made of a non-glare glass to make the LCD screen 129 easily visible to the user of the mobile workstation 100.

The LCD screen 129 can be coupled to the central control unit 125. The user of the mobile workstation 100 can perform various workstation functions by interacting with the touch sensitive LCD screen 129. In some example configurations, the upper surface 139 of the control unit housing 128 can be inclined towards the user to improve the visibility of the contents of the LCD screen 129.

Figure 5:
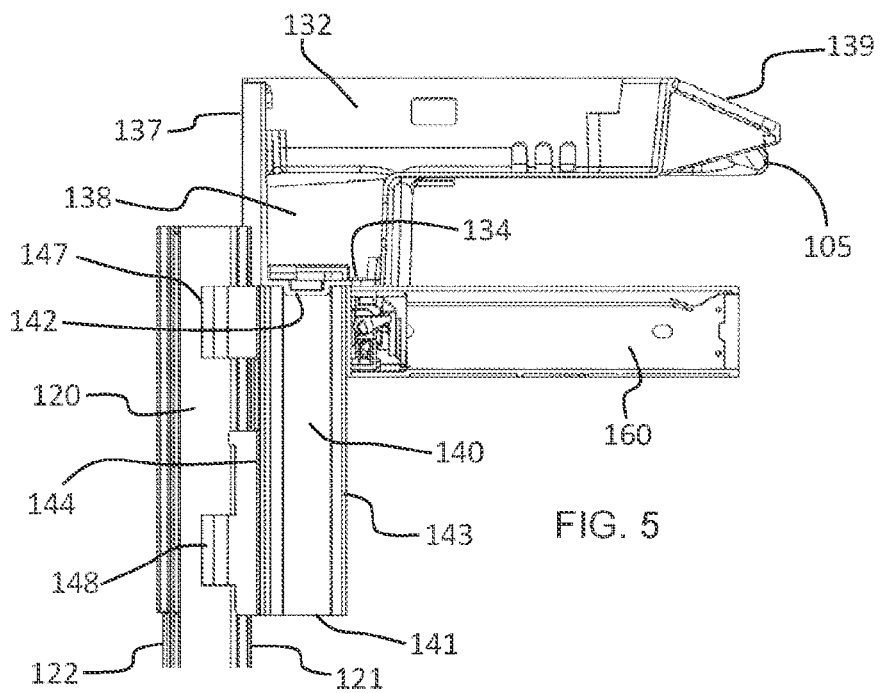
FIG. 5 illustrates a cross-sectional view of a sub-assembly of the mobile workstation of FIG. 1B, according to an example configuration of the present disclosure.
Figure 8:
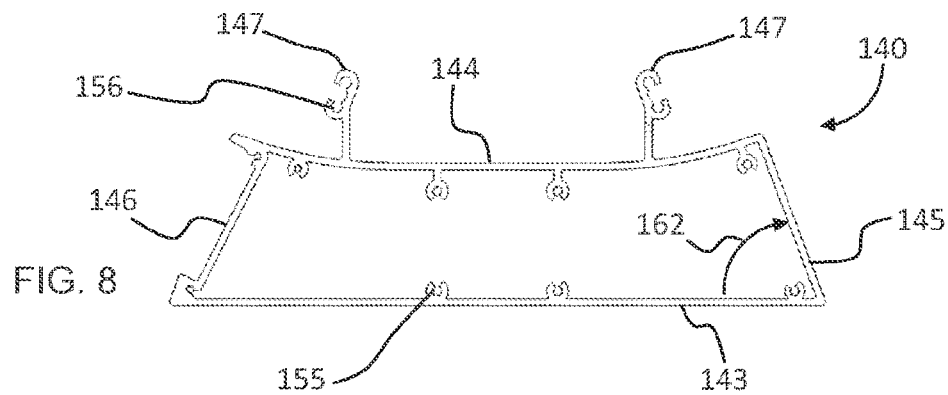
FIG. 8 illustrates the top view of the cable storage box, according to an example configuration of the present disclosure.

FIGS. 5 and 6 are a cross-sectional view and a perspective view of a sub-assembly including the cable storage box 140, the drawer housing 160, and the computer storage compartment 132 of the mobile workstation 100 of FIG. 1B, respectively. The cable storage box 140 can include a front wall 143 and a rear wall 144 opposite the front wall 143. A right wall 145 and a left wall 146 opposite the right wall 145 can connect the front wall 143 and the rear wall 144. In some example configurations, the right wall 145 and the left wall 146 can have an angle 162 relative to the front wall 143 as illustrated in FIG. 8. The front wall 143, the rear wall 144, the right wall 144, and the left wall can form an interior space of the cable storage box 140.

The cable storage box 140 can be elongated in a vertical direction from a lower end 141 to an upper end 142. The rear wall 144 of the cable storage box 140 can be located in close proximity to the support structure 120. One or more upper extension arms 147 and one or more lower extension arms 148 can be built into the rear wall 144. In some example configurations, the upper extension arms 147 and the lower extension arms 148 can be connected to each other to form a single elongated extension arm.

The upper extension arm 147 and the lower extension arm 148 can be inserted in an interior space of the support structure 120 through an opening located on the front face 121 of the support structure 120, and they can be coupled to the support structure 120 as it will be discussed below in this disclosure. In some example configurations, the rear wall 144, the upper 147 and the lower 148 extension arms of the cable storage box 140 can form the moving bracket. The counterbalance mechanism 115 of FIG. 2 can be coupled between the support structure 120 and the moving bracket (e.g., cable storage box 140). The cable storage box 140 can move along at least a portion of the support structure 120 to adjust a height of the cable storage box 140 (e.g., adjust a distance between the cable storage box 140 and the base 110 of the mobile workstation 100). Similarly, the height of any components that are coupled to the cable storage box 140 (e.g., the computer storage compartment 132, or the drawer housing 160) can also be adjusted as the height of the cable storage box 140 is adjusted.

The bottom surface 134 of the recessed section 138 of the computer storage compartment 132 can be rested against the upper end 142 of the cable storage box 140. The computer storage compartment 132 can be coupled to the upper end 142 of the cable storage box 140 using known mechanical attachment methods (e.g., screws).

A cap 149 can be coupled to the lower end of the cable storage box 140. The lower end 141 of the cable storage box 140 can be covered by the cap 149, and the upper end 142 of the cable storage box 140 can be covered by the computer storage compartment 132 to completely enclose the interior space of the cable storage box 140. The drawer housing 160 can be coupled to the front wall 143 of the cable storage box 140 as described below.

FIG. 7 is a top view of the sub-assembly of FIG. 5. The rear wall 137 of the computer storage compartment 132 can be located in close proximity to the support structure 120. The cable storage box 140 is hidden under the computer storage compartment 132 in FIG. 7. However, the upper extension arms 147 extending away from the rear wall 144 of the cable storage box 140 are visible. The upper extension arms 147 can be inserted into the internal space of the support structure 120 through one or more openings on the front face 121 of the support structure 120 as illustrated in FIG. 7.

The recessed section 138 of the computer storage compartment 132 can at least partially overlap with the cable storage box 140. The upper end 142 of the cable storage box 140 can be in contact with the bottom surface 134 of the recessed section 138 of the computer storage compartment 132. One or more apertures 126 can be formed on the bottom surface 134.

Figure 9:
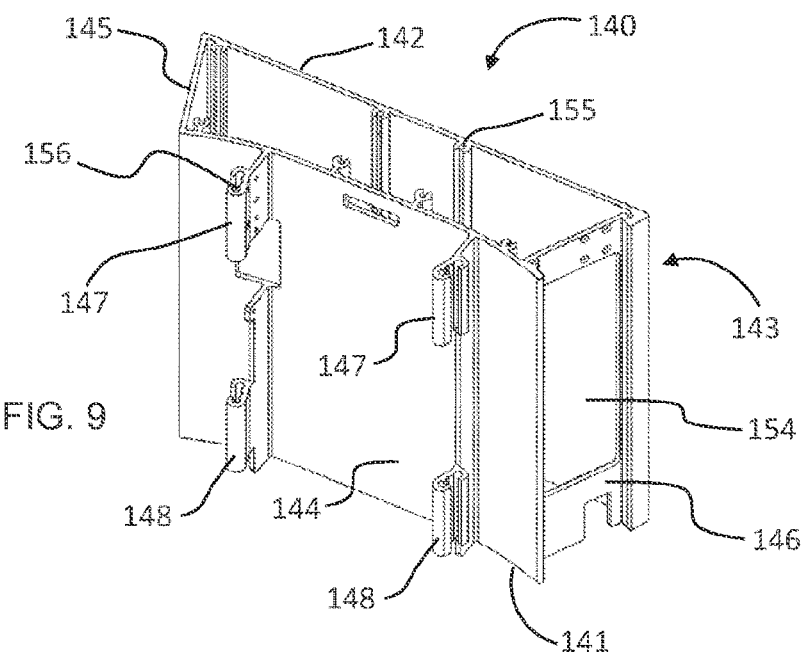
FIG. 9 illustrates the perspective view of the cable storage box of FIG. 8, according to an example configuration of the present disclosure.

FIGS. 8 and 9 are the top view and the perspective view, respectively, of the cable storage box 140 of FIG. 5 according to an example configuration of the current disclosure. The upper extension arm 147 and the lower extension arm 148 can be formed as an integral part of the cable storage box 140. The upper 147 and the lower 148 extension arms can be connected via the rear wall 144 of the cable storage box 140. One or more first mounting holes 155 can be formed as part of the cable storage box. The one or more first mounting holes 155 can be used to couple the computer storage compartment 132 to the cable storage box 140. The one or more apertures 126 located on the computer storage compartment 132 can align with the one or more first mounting holes 155 located on the cable storage box 140, and one or more screws (not shown in FIG. 7) can be inserted through the one or more apertures 126 to threadingly engage with the one or more first mounting holes 155 to securely couple the computer storage compartment 132 to the cable storage box 140. The cable storage box 140 can further include one or more second mounting holes 156 that can be formed as part of the upper 147 and lower 148 extension arms. The one or more second mounting holes 156 can be used to couple the cable storage box 140 to the support structure 120.

Figure 14:
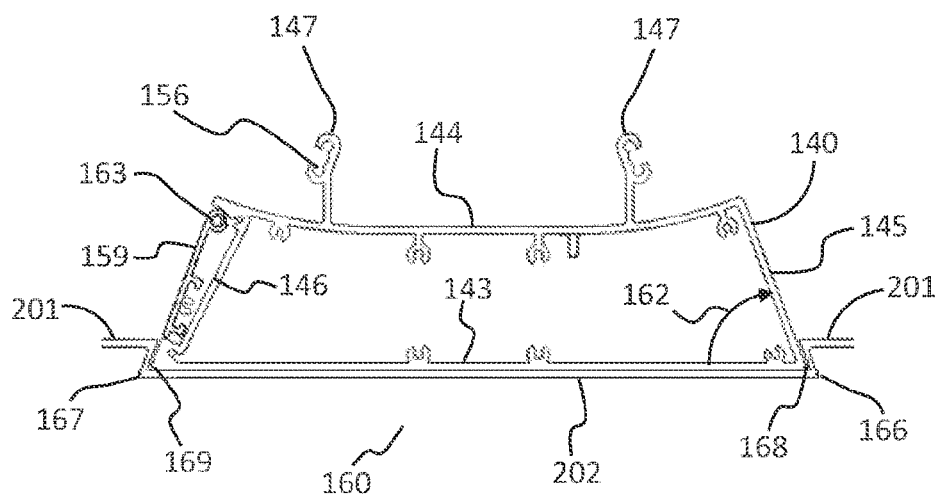
FIG. 14 illustrates the coupling between the cable storage box of FIG. 13A and the drawer housing of FIG. 13B, according to an example configuration of the present disclosure.

In some example configurations, there can be an opening on one or both of the right wall 145 and the left wall 146 of the cable storage box 140 (e.g., opening 154 located on the left side wall 146). The opening 154 can allow the user to access the content of the cable storage box 140. In some example configurations, a door 159 can be coupled to the cable storage box 140 where the opening 154 is located (e.g., the door 159 can be rotatingly coupled with the cable storage box 140 at a hinge 163 as illustrated in FIG. 14). The door 159 can selectively allow access to an interior space of the cable storage box 140 through the opening 154. A lock (not shown) can be used to lock the door 159 to prevent it from opening by unauthorized users.

Figure 10:
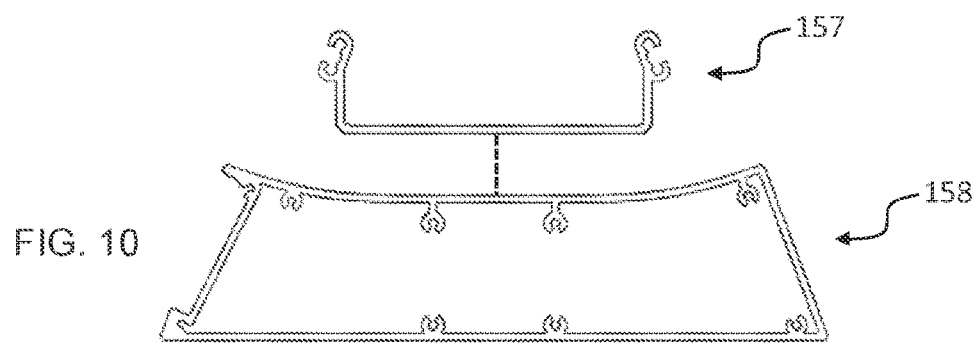
FIG. 10 illustrates an exploded view of a moving bracket and a cable storage box, according to an example configuration of the present disclosure.

In some example configurations, the moving bracket 157 and the cable storage box 158 can be formed independently as illustrated in FIG. 10. The moving bracket 157 and the cable storage box 158 can be coupled during the assembly process, e.g., as a sub-assembly.

Figure 11:
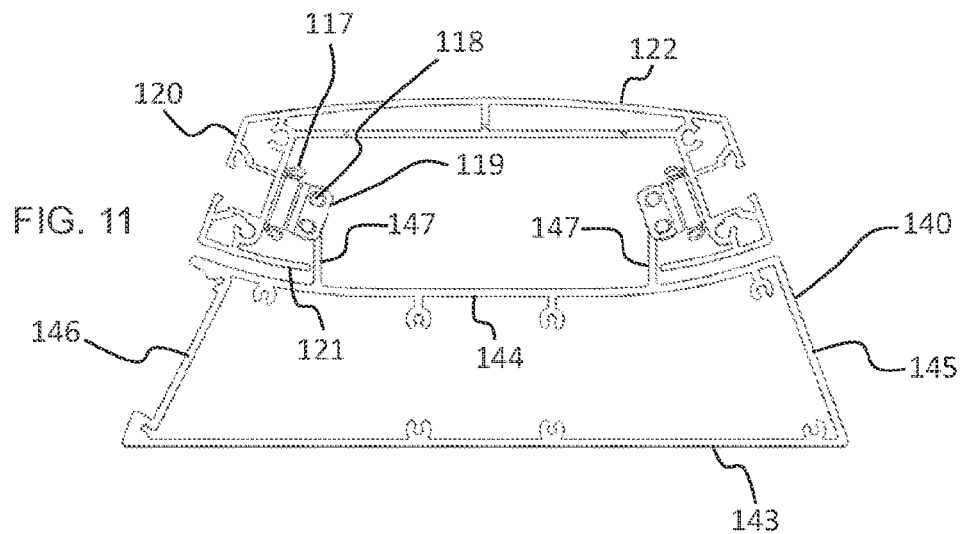
FIG. 11 illustrates the top view of the sub-assembly of the cable storage box and the support structure, according to an example configuration of the present disclosure.
Figure 12:
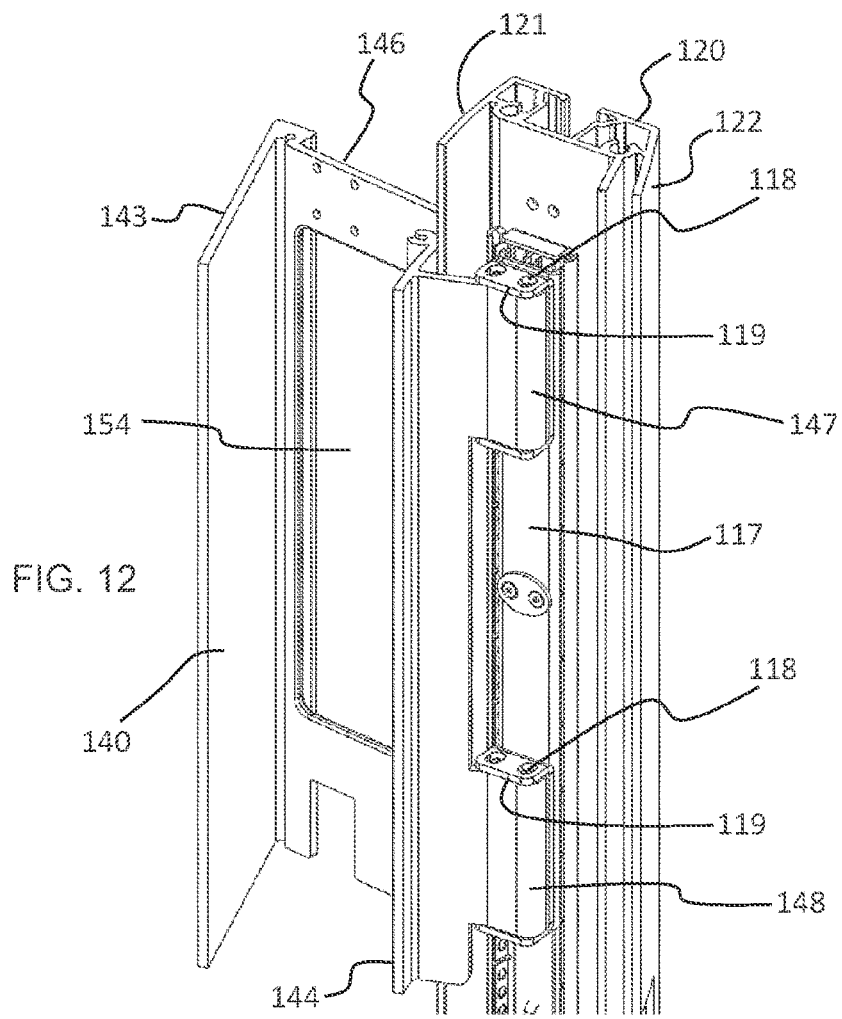
FIG. 12 illustrates cutaway perspective view of the sub assembly of the cable storage box and the support structure of FIG. 11, according to an example configuration of the present disclosure.

FIGS. 11-12 are the top view and perspective cutaway view of the sub-assembly of the cable storage box 140 and the support structure 120, respectively. Sections of the cable storage box 140 and the support structure 120 are removed in FIG. 12 to show the coupling between the cable storage box 140 and the support structure 120. One or more elongated gliders 117 (e.g., a ball slide) can be coupled to the support structure 120. The one or more gliders 117 can be elongated in the longitudinal direction of the support structure 120. The one or more upper extension arms 147 and the one or more lower extension arms 148 can be inserted into an interior space of the support structure 120 and they can be coupled to the one or more gliders 117.

The sub-assembly of the cable storage box 140 and the support structure 120 shown in FIG. 12 can further include one or more U-shaped connecting brackets 119. The one or more U-shaped connecting brackets 119 can be coupled to the glider 117. The one or more U-shaped connecting brackets 119 can capture the upper and lower ends of the upper extension arm 147 and the lower extension arm 148 as illustrated in FIG. 12. At least one aperture 118 can be formed on the U-shaped connecting bracket 119. A screw (not shown) can be inserted through at least one aperture 118 and threadingly engage with the one or more second mounting holes 156 that are located on the upper 147 and lower 148 extension arms. Through the sub-assembly of FIG. 12, the cable storage box 140 can be coupled to the support structure 120. The cable storage box 140 can move along at least a portion of the support structure 120.

Figure 13A:
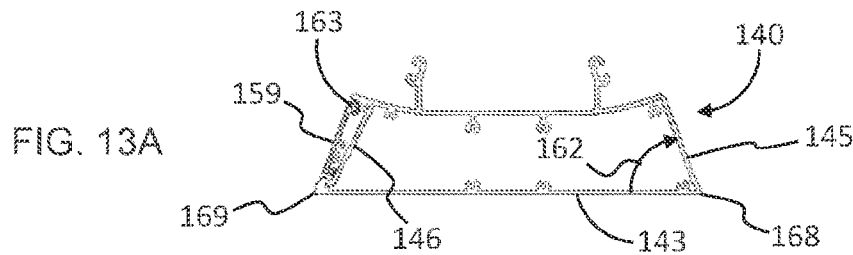
FIG. 13A illustrates a top view of the cable storage box, according to an example configuration of the present disclosure.

FIG. 13A shows the top view of the cable storage box 140 according to an example configuration of the current disclosure. The right wall 145 and the left wall 146 of the cable storage box 140 can be inclined relative to the front wall 143. An angle 162 can be formed between the right wall 145 or the left wall 146 and the front wall 143 of the cable storage box 140. A right corner 168 can be located at the intersection of the right wall 145 and the front wall 143, and a left corner 169 can be located at the intersection of the right wall 146 and the front wall 143 of the cable storage box 140.

Figure 13B:
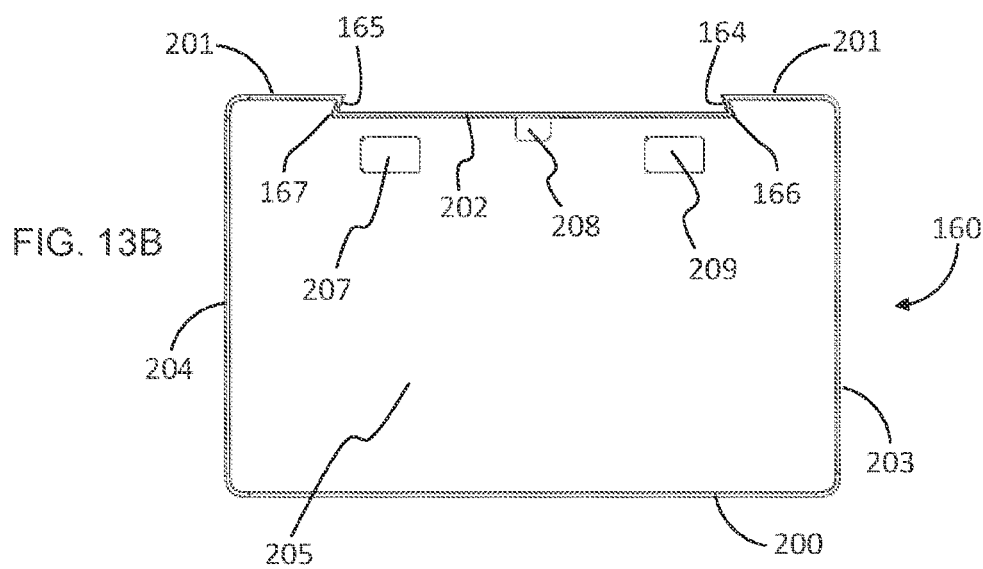
FIG. 13B illustrates a top view of the drawer housing, according to an example configuration of the present disclosure.

FIG. 13B shows the top view of the drawer housing 160 according to an example configuration of the current disclosure. The drawer housing 160 can have a front side 200, and a rear wall 201 opposite the front side 200. The rear wall 201 of the drawer housing 160 can include a recessed section 202. The recessed section 202 can be coupled to the rear wall 201 through a right connecting wall 164 and a left connecting wall 165. The right connecting wall 164 and the left connecting wall 165 can be angled relative to the rear wall 201. The angle between the right connecting wall 164 or the left connecting wall 165 and the rear wall 201 can be in general the same as the angle 162 of the cable storage box 140. A right corner 166 can be formed at the intersection of the right connecting wall 164 with the recessed section 202, and a left corner 167 can be formed at the intersection of the left connecting wall 165 with the recessed section 202.

Referring back to FIG. 6, the recessed section 202 and the right 164 and the left 165 connecting walls of the drawer housing 160 can be configured to receive the front wall 143 of the cable storage box 140. The front wall 143 of the cable storage box 140 can be inserted into the recessed section 202 of the drawer housing 160 proximate the lower end 141 of the cable storage box 140. The drawer housing 160 can slide along the cable storage box 140 starting from the lower end 141 towards the upper end 142. The drawer housing 160 can be secured to the cable storage box 140 at a desired location by means of mechanical fasteners as described below.

FIG. 14 is a close-up view of the coupling between the drawer housing 160 and the cable storage box 140. The front wall 143 of the cable storage box 140 can be configured to be inserted into the recessed section 202 of the drawer housing 160. In the coupled configuration, the front wall 143 of the cable storage box 140 can be located in close proximity against the recessed section 202 of the drawer housing 160. The right corner 168 of the cable storage box 140 can be located proximate the right corner 166 of the recessed section 202, and the left corner 169 of the cable storage box 140 can be located proximate the left corner 167 of the recessed section 202.

In the coupled configuration, the right wall 145 of the cable storage box 140 can be proximate the right connecting wall 164 of the drawer housing 160, and the left wall 146 of the cable storage box 140 can be proximate the left connecting wall 165 of the drawer housing 160. Together the right connecting wall 164 and the left connecting wall 165 can form a wedge shape that can prevent the recessed section 202 of the drawer housing 160 from moving in a direction perpendicular to the front wall 143 of the cable storage box 140 once the cable storage box 140 is inserted into the recessed section 202.

Figure 15:
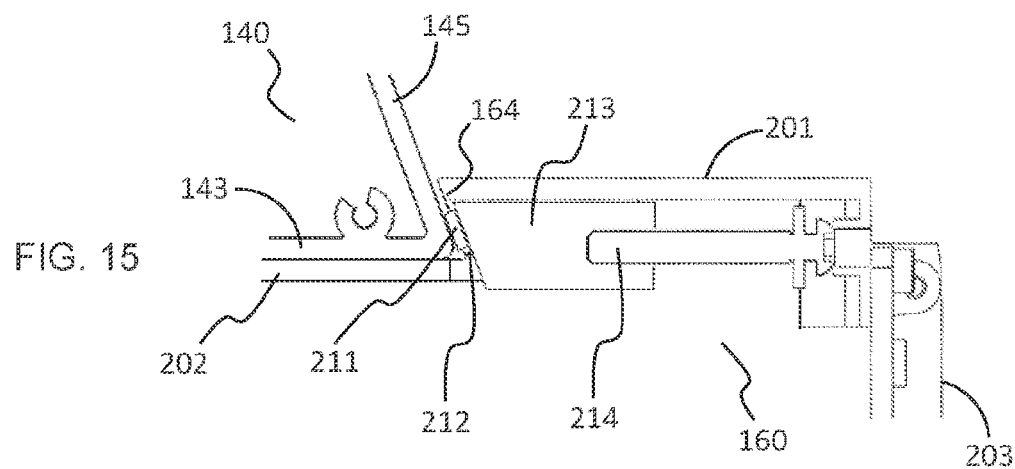
FIG. 15 illustrates a close-up view of the connection between the cable storage box of FIG. 13A and the drawer housing of FIG. 13B, according to an example configuration of the present disclosure.

FIG. 15 is a close-up partial view of the coupling between the cable storage box 140 and the drawer housing 160 according to an example configuration of the current disclosure. Only the right corner of the recessed section 202 and the cable storage box 140 are shown. The connection on the left side of the recessed section 202 can be similar. The front wall 143 of the cable storage box 140 can be inserted into the recessed section 202 between the right 164 and the left 165 connecting walls. The front wall 143 can be proximate the recessed section 202, and the side wall 145 of the cable storage box 140 can be proximate the right connecting wall 164.

In some example configurations, an opening 212 can be located over the one or both of the right 164 and the left 165 connecting walls. A latch 213 can be located behind the opening 212 on one or both sides of the recessed section 202. The latch 213 can be inside the drawer housing 160 proximate the rear wall 201. The latch 213 can be slidingly coupled to the drawer housing 160. A pad 211 can be located in the opening 212 on one or both of the right 164 and the left 165 connecting walls and coupled to the latch 213. The side walls 145 and 146 of the cable storage box 140 can be in contact with the pads 211. A screw 214 can be rotatingly coupled with the drawer housing 160 and threadingly engaged with the latch 213. The screw 214 can be rotated by the user of the drawer assembly 160 to move the latch 213 in the axial direction of the screw 214.

When the drawer housing 160 is coupled to the cable storage box 140 and slid into the desired location as described earlier, the screw 214 can be rotated to push the latch 213 towards the cable storage box so that the pad 211 coupled to the latch 213 can apply pressure to the side wall 145 of the cable storage box 140 to secure it in the desired location.

Figure 16A:
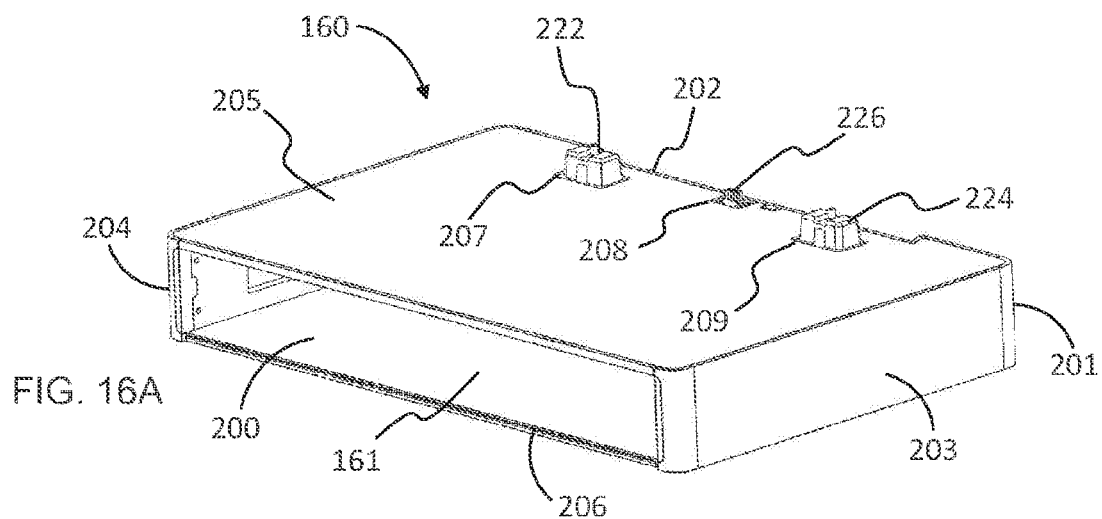
FIG. 16A illustrates a perspective view of the drawer housing, according to an example configuration of the present disclosure.
Figure 16B:
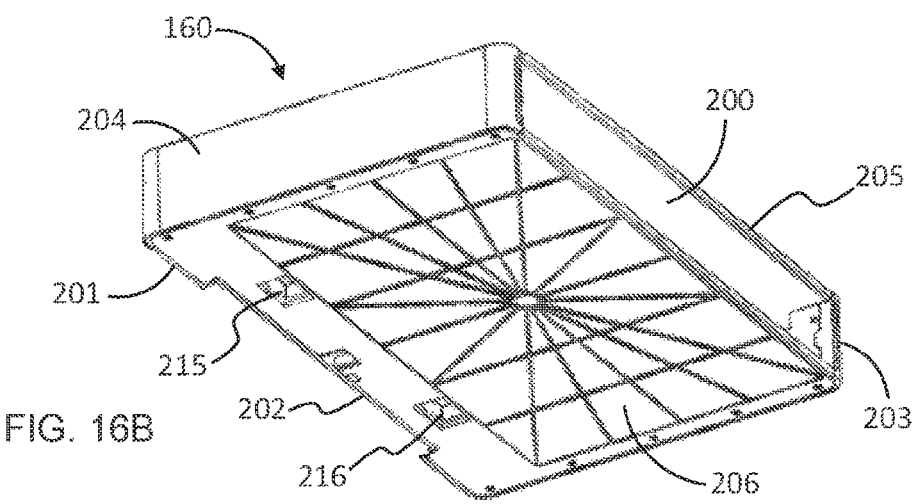
FIG. 16B illustrates a bottom perspective view of the drawer housing, according to an example configuration of the present disclosure.

FIGS. 16A and 16B are upper and lower perspective view of the drawer housing 160 according to an example configuration of the current disclosure. The drawer housing 160 can have a front side 200, a rear wall 201 opposite the front side 200, a right side 203 and a left side 204 opposite the right side 203. The drawer housing 160 can further include an upper surface 205 and a lower surface 206. The combination of the front side 200, the rear wall 201, the right side 203, the left side 204, the upper surface 205, and the lower surface 206 can form an interior space 161 of the drawer housing 160. In some example configurations, one or more drawers with various sizes and shapes can be inserted into the interior space 161 of the drawer housing 160 through the front side 200 as it will be discussed below.

The upper surface 205 of the drawer housing 160 can include a first opening 207, a second opening 208, and a third opening 209. The lower surface 206 of the drawer housing 160 can include a first recess 215 and a second recess 216

Figure 17:
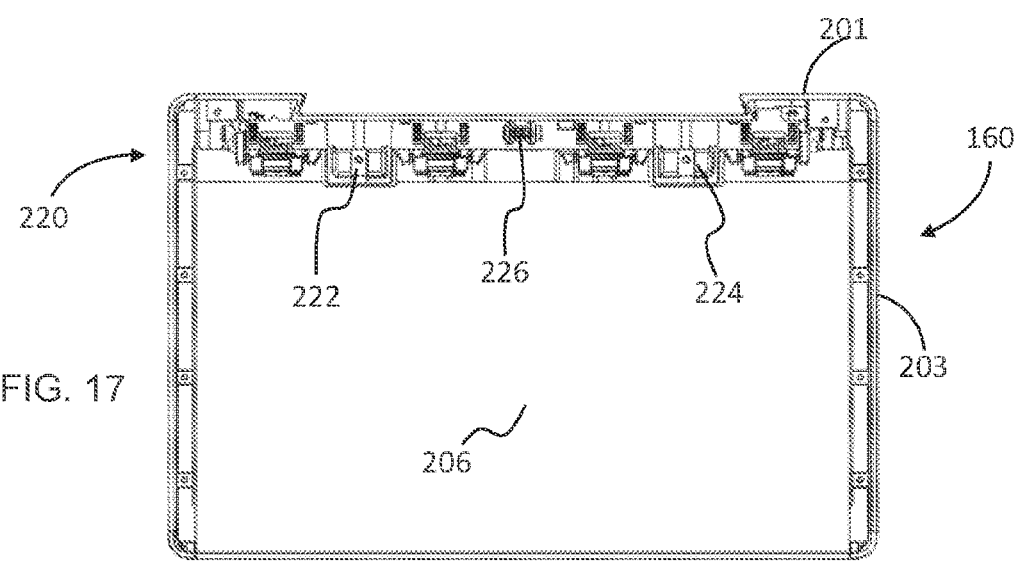
FIG. 17 illustrates a top view of the drawer housing, according to an example configuration of the present disclosure.

FIG. 17 is a top view of the drawer housing 160. The top surface 205 of the drawer housing is removed to show the components under it. The drawer housing 160 can include a lock assembly 220. The lock assembly 220 can include a first mechanical connector 222 and a second mechanical connector 224 and an electrical connector 226.

Referring to FIG. 16A, the first 222 and the second 224 mechanical connectors can protrude through the first opening 207 and the third opening 209, respectively. The electrical connector 226 can protrude through the second opening 208. The mechanical connectors 222 and 224, and the electrical connector 226 can connect the drawer housing 160 to the mobile workstation 100 of FIG. 1B as it will be discussed below.

Figure 18:
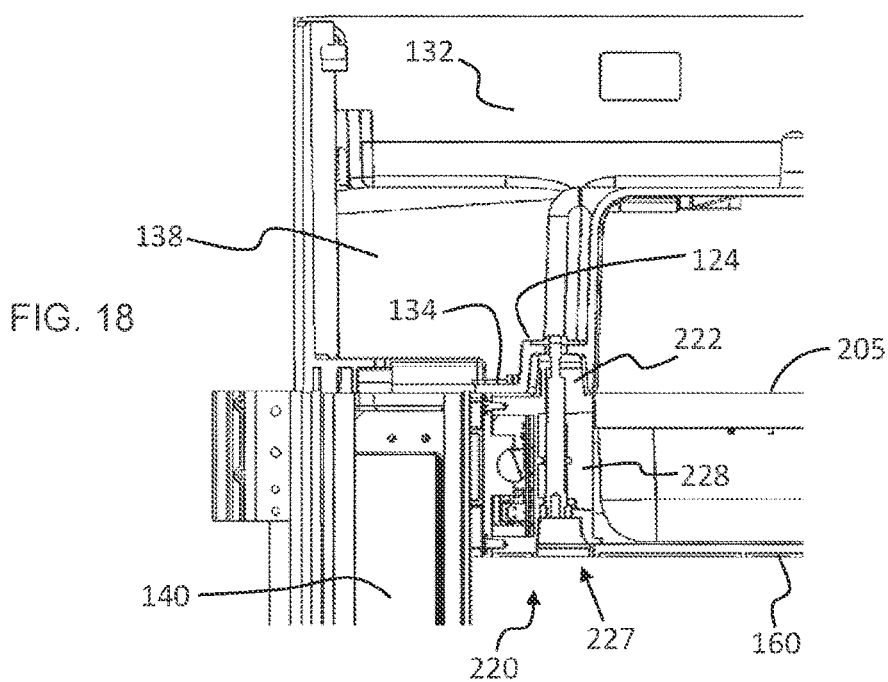
FIG. 18 illustrates a cross-sectional view of the coupling between the drawer housing and the computer storage compartment, according to an example configuration of the present disclosure.

FIG. 18 is a cross-sectional view of the connection between the drawer housing 160 and the computer storage compartment 132 according to an example configuration of the current disclosure. As shown in FIG. 16A, the upper end of the one or more mechanical connectors 222 and 224 extend above the upper surface 205 of the drawer housing 160. In the coupled configuration (e.g., the drawer housing 160 is coupled to the cable storage box 140 and slid towards the computer storage compartment 132), the one or more mechanical connectors 222 and 224 can align with the one or more recesses 124 located on the bottom surface 134 of the recessed section 138 of the computer storage compartment 132. A connector assembly 227 can be coupled to the mechanical connectors 222 and 224. The connector assembly 227 can include a stud 228. The stud 228 can be used to further secure the drawer housing 160 on to the mobile workstation 100 of FIG. 1B.

Figure 19:
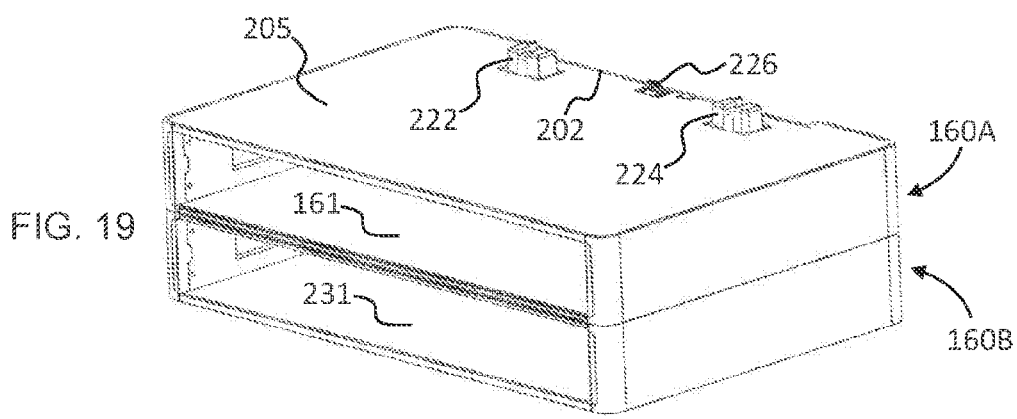
FIG. 19 illustrates two drawer housings coupled in stacked configuration, according to an example configuration of the present disclosure.

FIG. 19 shows a first drawer housing 160A and a second drawer housing 160B in a stacked configuration according to an example configuration of the current disclosure. Construction of the first drawer housing 160A and the second drawer housing 160B are the same as the construction of the drawer housing 160 discussed earlier. The first drawer housing 160A can be coupled to the cable storage box 140, and it can be further secured to the computer storage compartment 132 through the one or more mechanical connectors 222 and 224 as shown in FIG. 18. The second drawer housing 160B can also have one or more connectors similar to the mechanical connectors 222 and 224 of the first drawer housing 160A. The second drawer housing 160B can be coupled to the cable storage box 140 and further secured to the first drawer housing 160A through the one or more connectors located on the second drawer housing 160B.

Figure 20A:
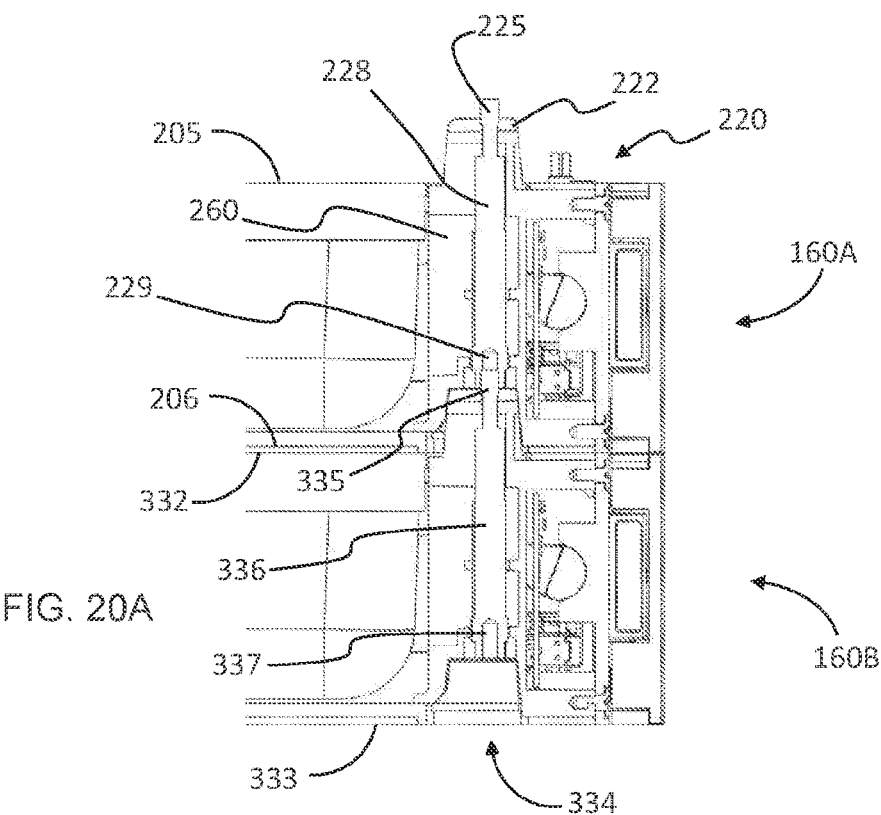
FIG. 20A illustrates a cross-sectional view of the coupling between two drawer housings of FIG. 19, according to an example configuration of the present disclosure.

FIG. 20A is a cross-sectional view of the coupling between the first drawer housing 160A and the second drawer housing 160B according to an example configuration of the current disclosure. A stud 228 can be located inside the one or more mechanical connectors 222 and 224 of the first drawer housing 160A. The stud 228 can have a threaded shaft 225 located proximate to its upper end. The stud 228 can further have a threaded hole 229 located proximate to its lower end. The stud 228 can be rotatingly coupled with the mechanical connectors. In the coupled configuration as shown in FIG. 18 according to an example configuration of the current disclosure, the one or more mechanical connectors 222 and 224 can align with the one or more recesses 124 located on the bottom surface 134 of the recessed section 138 of the computer storage compartment 132, and the upper end 225 of the stud 228 can threadingly engage with the computer storage compartment 132 to further secure the first drawer housing 160A on to the mobile workstation 100 of FIG. 1B.

After the first drawer housing 160A is coupled to the mobile workstation 100, the second drawer housing 160B can be coupled to the cable storage box 140. The lower end of the cable storage box 141 can be inserted into the recessed section 202 of the second drawer housing 160B. The second drawer housing 160B can be pushed up towards the first drawer housing 160A such that the upper surface 332 of the second drawer housing 160B can rest against the lower surface 206 of the first drawer housing 160A as illustrated in FIG. 20A. The one or more mechanical connectors 222 and 224 of the second drawer housing 160B can be used to secure the second drawer housing 160B to the first drawer housing 160A.

A stud 336 can be located inside the mechanical connectors 222 and 224 of the second drawer housing 160B. The stud 336 can have a threaded shaft 335 located proximate to its upper end. The stud 336 can further have a threaded hole 337 located proximate to its lower end. The stud 336 can be rotatingly coupled with the mechanical connectors 222 and 224 of the second drawer housing 160B. In the coupled configuration as shown in FIG. 20A, the one or more mechanical connectors of the second drawer housing 160B can align with the first recess 215 and the second recess 216 located at the lower surface 206 of the first drawer housing 160A. The lower end of the stud 336 can be accessed through an opening 334 located at the lower surface 333 of the second drawer housing 160B. The stud 336 can be rotated so that the upper end 335 of the stud 336 can threadingly engage with the threaded hole 229 proximate the lower end of the stud 228 located inside the mechanical connectors 222 and 224 of the first drawer housing 160A to further secure the second drawer housing 160B on to the mobile workstation 100.

Figure 20B:
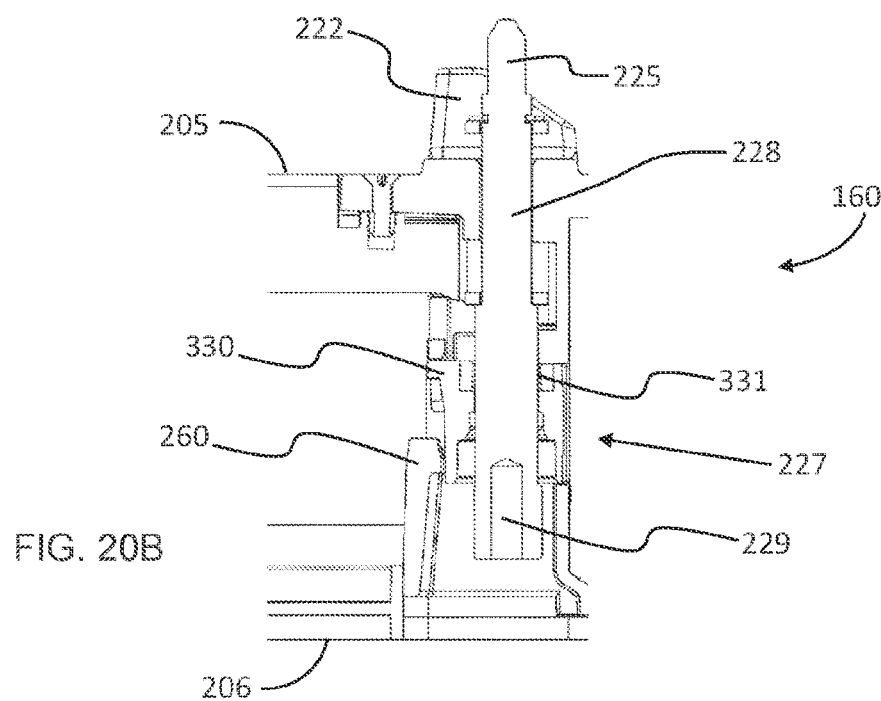
FIG. 20B illustrates a cross-sectional view of the connection assembly of a drawer housing, according to an example configuration of the present disclosure.

FIG. 20B is a cross-sectional view of the connector assembly 227 of the drawer housing 160 according to an example configuration of the current disclosure. The connector assembly 227 can include a slider 330 and a spring 331 (e.g., a compression spring). The slider 330 and the spring 331 can be concentric with the stud 228, and they can be movable relative to the stud 228. The slider 330 can have keying features (not shown in FIG. 20B) to engage with the holding block 260 and the stud 228.

The spring 331 can have an extended configuration and a contracted configuration. The spring 331 can be biased towards an extended configuration. In the extended configuration, the spring 331 can push the slider 330 towards the lower end of the stud 228, and the slider 330 can be keyed into the holding block 260 and to the stud 228 at the same time so that the stud 228 can be prevented from turning. This is useful when a second drawer housing 160B is coupled to the first drawer housing 160A as illustrated in FIG. 20A.

When the second drawer housing 160B is coupled to the first drawer housing 160A, the mechanical connector, and thus, the upper end of the stud 336 of the second drawer housing 160B can be placed inside at least one of the first recess 215 and the second recess 216 of the first drawer housing 160A. The upper end of the stud 336 can threadingly engage with the lower end of the stud 228. The stud 336 can be rotated to fasten the second drawer housing 160B to the first drawer housing 160A. During this fastening operation, it is desirable for the stud 228 to be prevented from rotating. The slider 330 can prevent the stud 228 from rotating as explained above.

In other applications, the stud 228 located inside the first drawer housing 160A needs to be rotated (e.g., during connecting or disconnecting the first drawer housing 160A from the workstation 100). The slide 330 can be pushed against the spring 331 towards the upper end of the stud 228 to disengage the keying features of the slider 330 from the holding block 260 and the stud 228. Once the keying features are disengaged, the stud 228 can be rotated freely.

In other example configurations, additional drawer housings can be coupled to the mobile workstation similarly as explained above.

Figure 21:
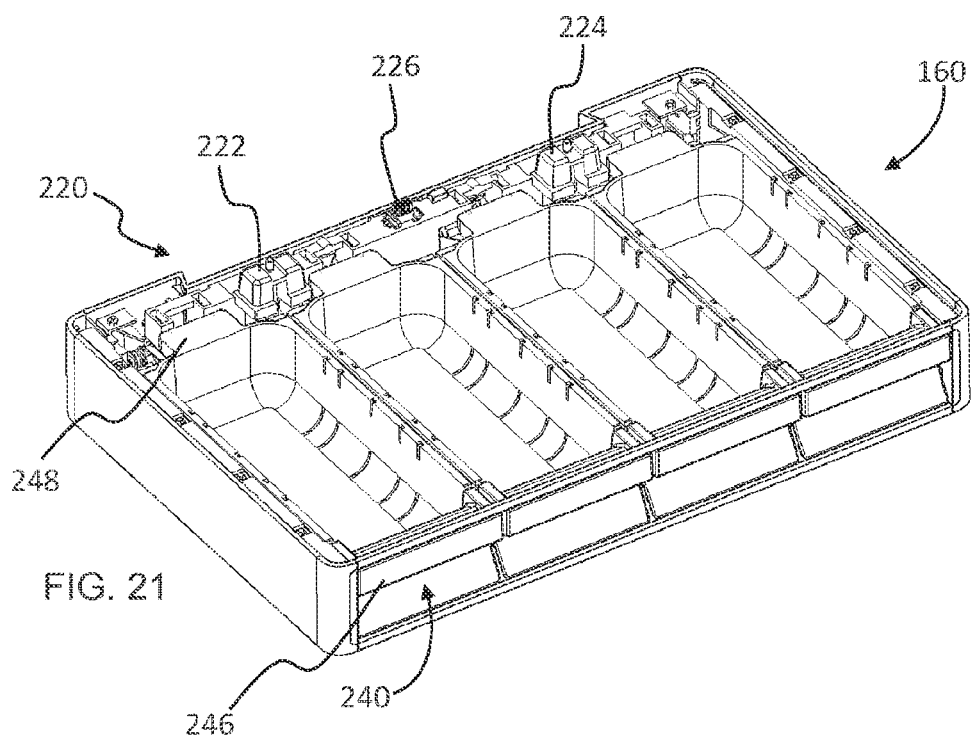
FIG. 21 illustrates a drawer housing with four single-stall drawers, according to an example configuration of the present disclosure.

FIG. 21 is a drawer housing 160 having four single-stall drawers 240 (shown in FIG. 26) according to an example configuration of the current disclosure. The upper surface of the drawer housing 160 is removed to show the drawers 240 located inside the drawer housing 160. The drawer housing 160 can be sized and shaped to receive the one or more drawers 240. The one or more drawers 240 can be inserted into the drawer housing 160 from the front side 200, and they can slide relative to the drawer housing 160. The lock assembly 220 can be located proximate the rear end of the drawer housing 160. The drawer 240 can include a lock tab 248 located proximate its rear end. The lock tab 248 can engage with the lock assembly 220 when the drawer 240 is fully inserted into the drawer housing 160.

Figure 22:
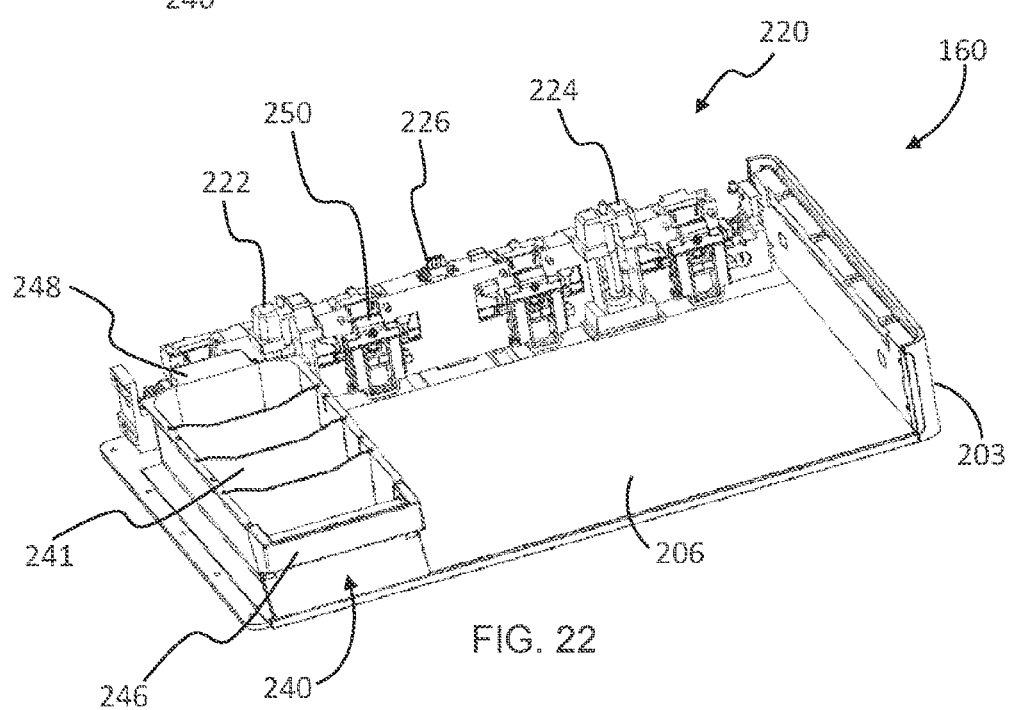
FIG. 22 illustrates a drawer housing with one single-stall drawer, according to an example configuration of the present disclosure.

FIG. 22 is a drawer housing 160 with one single-stall drawer 240. Upper and left side surfaces of the drawer housing 160, and additional drawers are removed to display the internal components of the drawer housing 160. The lock assembly 220 can include one or more latches 250. The one or more latches 250 can be in-line with the lock tab 248 of the one or more drawers 240 located inside the drawer housing 160. The one or more latches 250 can be activated by the user of the workstation 100 so that latches 250 can selectively engage or disengage with the lock tab 248 of each drawer 240 to secure them inside the drawer housing 160 or allow them to be at least partially pulled out of the drawer housing 160 to expose their content.

In some example configurations, one or more dividers 241 can be inserted into the drawer 240 to partition the internal space of the drawer 240. This can be useful to store various items in their own dedicated space to prevent them mixing up with other items (e.g., various medication).

Figure 23:
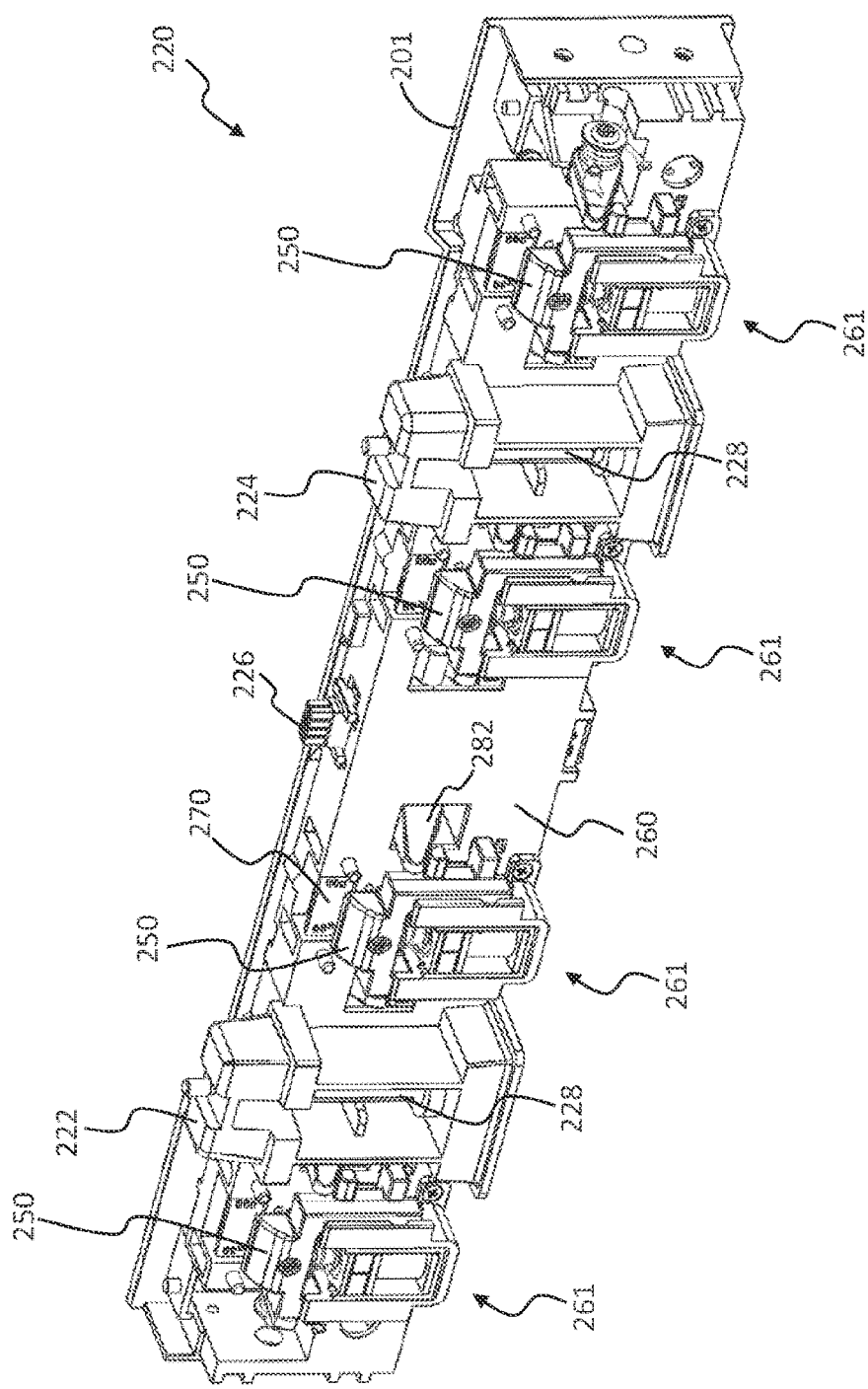
FIG. 23 illustrates a close-up view of the drawer lock assembly, according to an example configuration of the present disclosure.

FIG. 23 is a close-up view of the lock assembly 220 of FIG. 22. Lock assembly 220 can be located inside the drawer housing 160 proximate the rear wall 201. The lock assembly 220 can include a holding block 260 and a drawer controller 270. The drawer controller 270 can be coupled to the holding block 260. The one or more mechanical connectors 222 and 224 can be formed as an integral part of the holding block 260. An electrical connector 226 can be coupled to the holding block 260 and it can be electrically connected to the drawer controller 270.

The lock assembly 220 can further include one or more latches 250. The one or more latches 250 can be coupled to the holding block 260 via one or more solenoid mounting assemblies 261.

Figure 24:
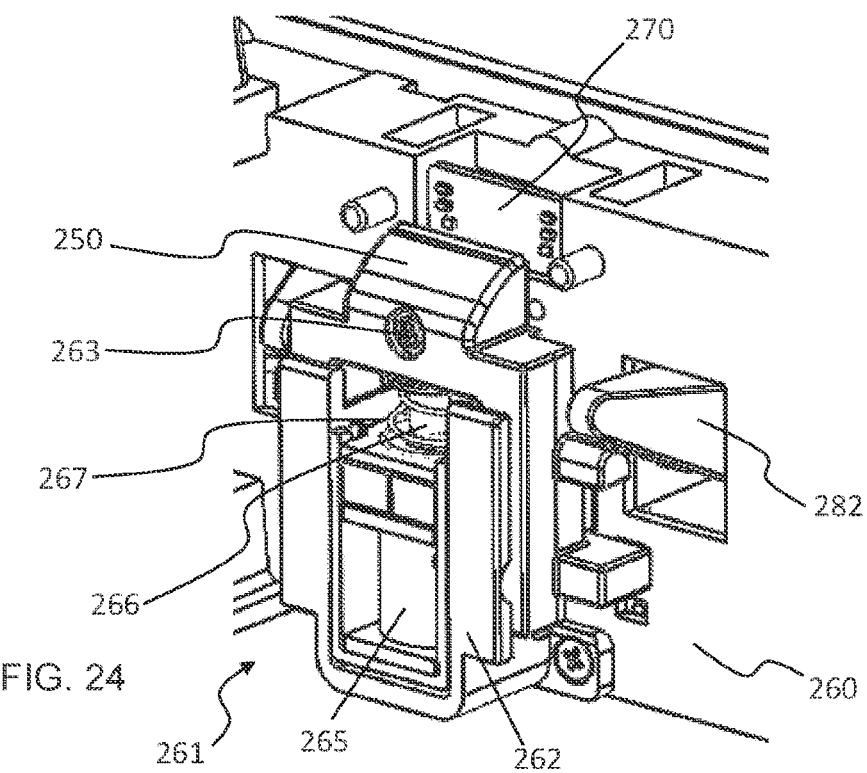
FIG. 24 illustrates a perspective view of a solenoid mounting assembly, according to an example configuration of the present disclosure.

FIG. 24 is a perspective view of a solenoid mounting assembly 261. In an example configuration, the solenoid mounting assembly 261 can include a solenoid housing 262, a solenoid body 265, a solenoid rod 266, and a compression spring 267. The solenoid housing 262 can be coupled to the holding block 260. The solenoid housing 262 can hold the solenoid body 265. A solenoid rod 266 can be slidingly engaged with the solenoid body 265. The solenoid rod 266 can move between an extended configuration and contracted configuration. The latch 250 can be coupled to the solenoid rod 266 and it can move relative to the solenoid body 265. The compression spring 267 can be concentric with the solenoid rod 266 and it can be located between the solenoid body 265 and the latch 250. The compression spring 267 biases the solenoid rod 266 towards the extended configuration. In the extended configuration, the latch 250 can be located further away from the solenoid body 265 compared to the contracted configuration.

Figure 25:
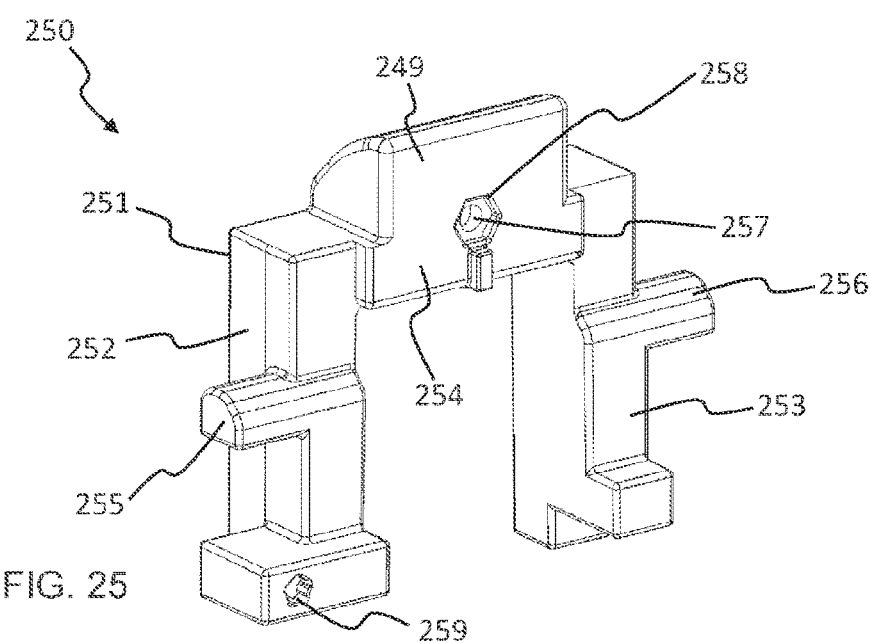
FIG. 25 illustrates a perspective view of a latch, according to an example configuration of the present disclosure.

FIG. 25 is a perspective view of the latch 250 according to an example configuration. The latch 250 can include a U-shaped latch body 251 including a first side 252, a second side 253 opposite the first side 252, and a base 254 connecting the first side 252 and the second side 253.

One or more latch arms (e.g., a first latch arm 255 and a second latch arm 256) can be coupled to one or more sides of the U-shaped latch body (e.g., the first latch arm 255 can be coupled to the first side 252 and the second latch arm 256 can be coupled to the second side 253). A tongue 249 can be coupled to the base 254 of the U-shaped latch body 251. The tongue 249 can be configured to engage with the lock tab 248 of the drawer 240 to secure it inside the drawer housing 160.

In an example configuration, the solenoid body 265 and the solenoid rod 266 can be located between the first side 252 and the second side 253 of the U-shaped latch body 251. The latch 250 can be coupled to the solenoid rod 266 and it can be configured to move with the solenoid rod 266. A hole 257 can be formed on the base 254 of the latch body 251, and a hexagonal shaped recess 258 can be formed around the hole 251 on one side of the latch body 251.

Figure 26:
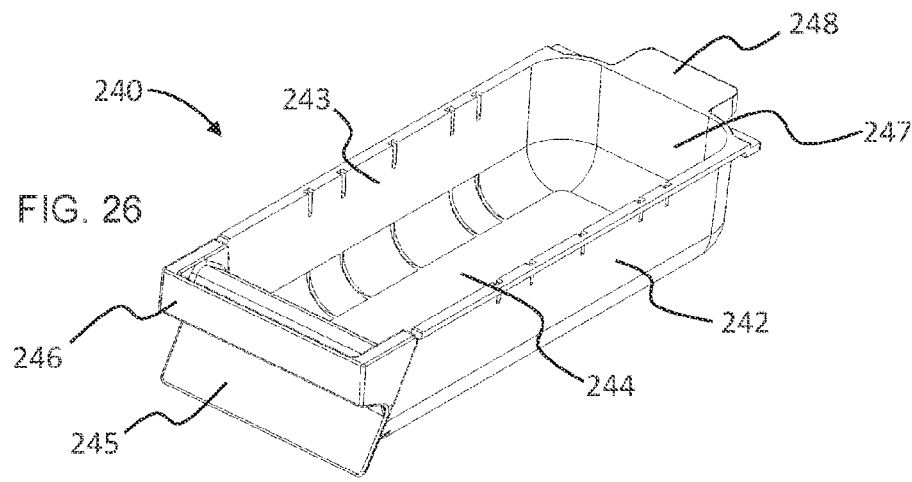
FIG. 26 illustrates front perspective views of a single-stall drawer, according to an example configuration of the present disclosure.

FIG. 26 is single-stall (e.g., small, narrow, or the like) drawers according to an example configuration of the current disclosure. A single-stall drawer 240 can be formed in a quadrilateral cross-section (e.g., rectangular, square, or the like) having a right-side wall 242, a left-side wall 243, a bottom surface 244, a front surface 245 and a rear surface 247. Upper surface (e.g., opposite the bottom surface 244) of each drawer 240 can be open to allow storage of items inside the drawer 240. A handle 246 can be formed into the front surface 245 and a lock tab 248 can be formed into the rear surface 247 of the drawer 240.

Figure 27:
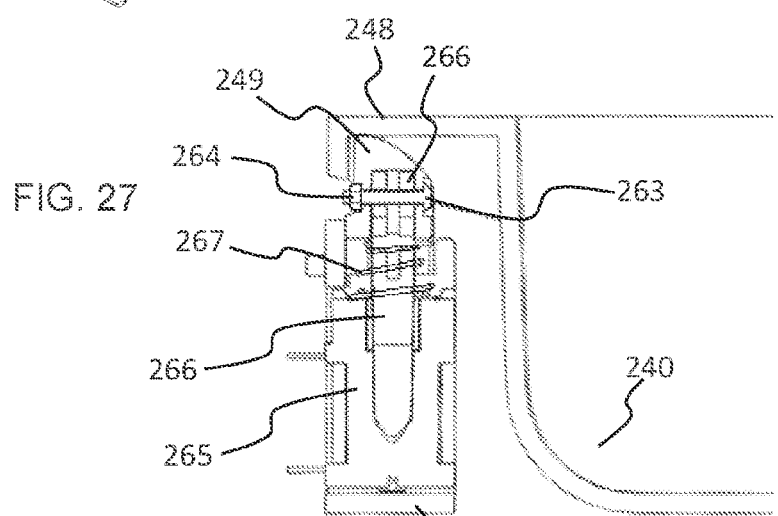
FIG. 27 illustrates a cross-sectional view of the coupling between the latch and the solenoid, according to an example configuration of the present disclosure.

FIG. 27 is a cross-sectional view of the coupling between the latch 250 and the solenoid rod 266. The upper end of the solenoid rod 266 can be inserted into the base 254, and a screw 263 can be inserted through the hole 257. The screw 263 can also engage with the solenoid rod 266 to connect the latch 250 to the solenoid rod 266. A nut 264 can be inserted into the hexagonal shaped recess 258 and the screw 263 can threadingly engage with the nut 264 to prevent it from backing out of the latch 250.

The compression spring 267 located between the latch 250 and the solenoid body 265 can bias the tongue 249 away from the solenoid body 265. In a locked configuration, the solenoid can be deactivated so that the compression spring 267 can push the tongue 249 away from the solenoid body 265 (e.g., the solenoid rod 266 can be in the extended configuration). In an unlocked configuration, the solenoid can be activated so that solenoid can pull the latch 250 and the tongue 249 towards the solenoid body 265 (e.g., the solenoid rod 266 can be in contracted configuration). When the drawer 240 is completely inserted into the drawer housing 160, the tongue 249 can engage with the lock tab 248 of the drawer 240 in the locked configuration as illustrated in FIG. 27.

Figure 28:
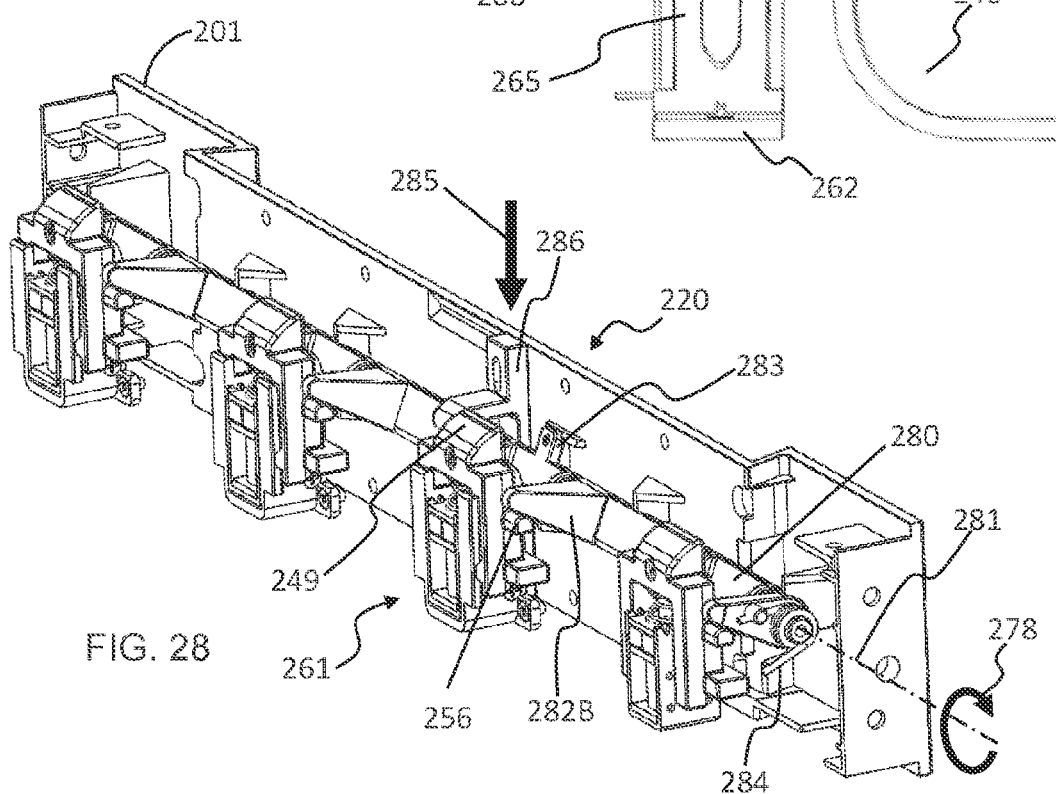
FIG. 28 illustrates a perspective view of the drawer lock assembly, according to an example configuration of the present disclosure.
Figure 29:
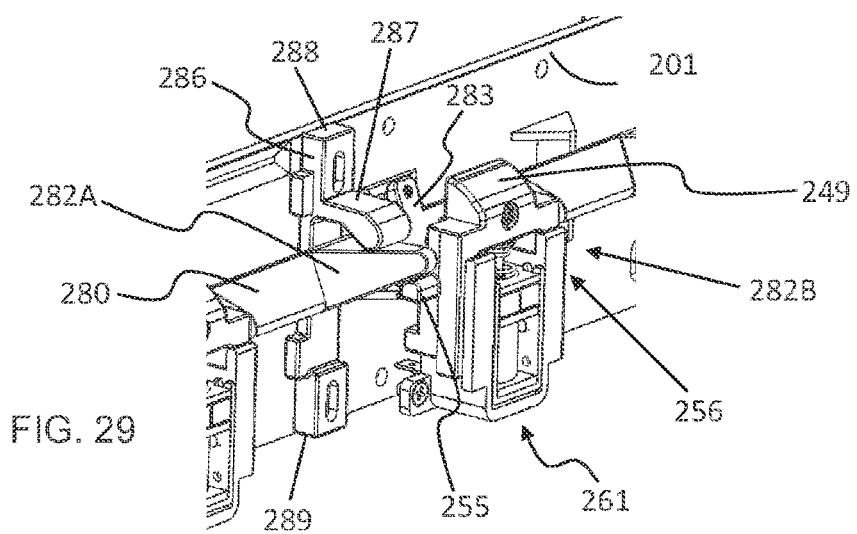
FIG. 29 illustrates a close-up partial perspective view of the drawer lock assembly of FIG. 28, according to an example configuration of the present disclosure.

FIG. 28 is a perspective view of the lock assembly 220 of FIG. 23, and FIG. 29 is a partial perspective view of the lock assembly 220 according to an example configuration of the current disclosure. The holding block 260 is removed from FIGS. 28-29 to show the internal components. The lock assembly 220 can include a manual release bracket 280. The manual release bracket 280 can have an elongated body (e.g., an elongated rod, elongated sheet metal bracket, or the like). The manual release brocket can be elongated in an axial direction 281. The manual release bracket 280 can be movingly (e.g., it can rotate, slide, shift, or the like) coupled to the holding block 260. In an example configuration, the manual release bracket 280 (e.g., an elongated rod) can rotate around the axis 281 relative to the holding block 260 as illustrated in FIGS. 28-29. The manual release bracket 280 can include one or more arms 282. The one or more arms 282 can protrude from the elongated body (e.g., elongated rod) of the manual release bracket 280 in a radial direction (e.g., perpendicular to the axis 281). The one or more arms 282 can rotate together with the manual release bracket 280 around the axis 281 (for example, rotate in a first direction 278).

In general, there can be one or more arms 282 associated with each solenoid mounting assemblies 261 (for example, the first arm 282A can be located proximate the left side of the solenoid mounting assembly 261 and the second arm 282B can be located proximate the right side of the solenoid mounting assembly 261). The first arm 282A and the second arm 282B can be configured to press on to the first latch arm 255 and the second latch arm 256, respectively.

The lock assembly can further include a spring 284 (e.g., a torsion spring, extension spring, compressions spring, leaf spring, or the like). The spring 284 can bias the one or more arms 282 of the manual release bracket 280 away from the latch arms 255 and 256. In an example configuration, the spring can be a torsion spring 284. The torsion spring 284 can be coaxial with the manual release bracket 280 (e.g., elongated rod). One leg of the torsion spring 284 can engage with the holding block 260, and the other leg of the torsion spring 284 can be coupled to the manual release bracket 280. The torsion spring 284 can rotate the manual release bracket 280 in the first direction 278 (e.g., the one or more arms 282 can be biased away from the latch arm 255). When the one or more arms 282 are away from the latch arms 255 and 256, the compression spring 267 can translate the latch (e.g., push the latch 250 upwards) such that the tongue 249 can engage with the lock tab 248 when the drawer 240 is completely inserted into the drawer housing 160.

In some example configurations, the lock assembly 220 can further include a slider 286. The slider 286 can be slidingly engaged with the holding block 260. In general, the slider 286 can have an elongated body (for example, the slider body can elongate between the upper end 288 and the lower end 289 of the slider 286). The slider 286 can be configured to move in a first direction 285. In general, the first direction 285 can be in vertical direction. The slider 286 can be manually (e.g., pushed, pulled, or the like) or electronically (e.g., via a servomotor, or the like) activated by the user of the workstation 100. The slider 286 can cooperate with the manual release bracket 280 to lock or unlock the drawers.

In some example configurations, the slider 286 can include a finger 287 as illustrated in FIGS. 28-29. The finger 287 can extend away from the slider body. The finger 287 can be configured to contact the one or more arms 282 (e.g., the finger 287 can apply pressure on the one or more arms 282). In the locked configuration of the lock assembly 220 (e.g., when the tongue 249 is engaged with the lock tab 248), if the solenoid malfunctions (e.g., solenoids cannot be activated to pull the latch 250 and the tongue 249 down towards the solenoid body 265 electronically) and the drawer 240 cannot be unlocked, the user of the workstation 100 can press on to the upper end 288 of the slider 286 to push it down so that the finger 287 can apply pressure on to the one or more arms 282 to rotate the manual release bracket 280 in a second direction opposite the first direction 278, and thus, the one or more arms 282 can push on to the latch arms 255 and 256 to push the latch 250 and the tongue 249 down towards the solenoid body 265 to unlock the drawers 240 manually.

Figure 30:
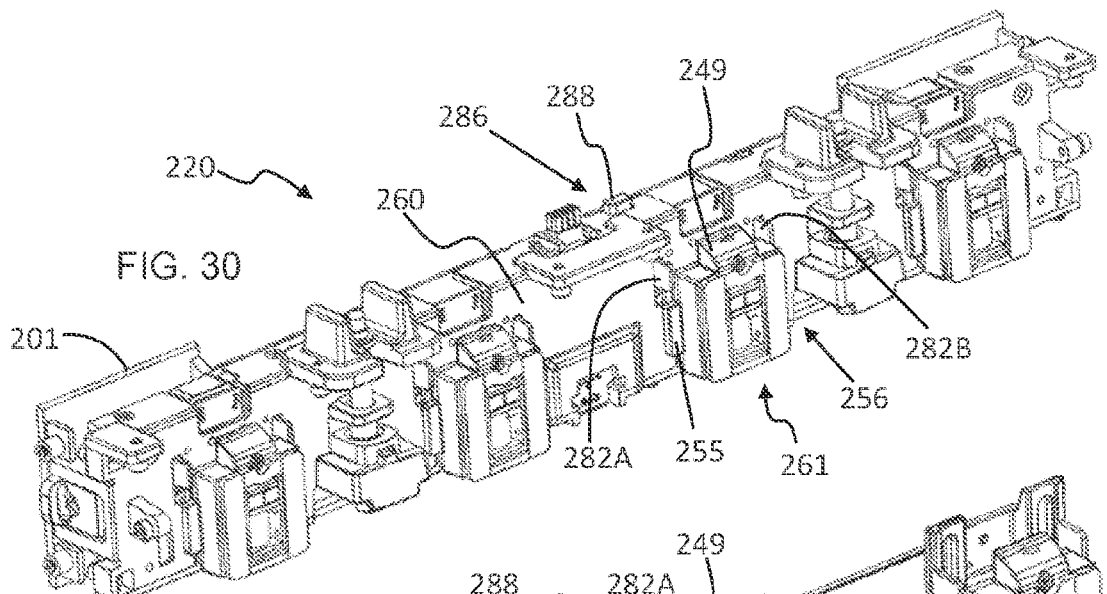
FIG. 30 illustrates a perspective view of a drawer lock assembly, according to an example configuration of the present disclosure.
Figure 31:
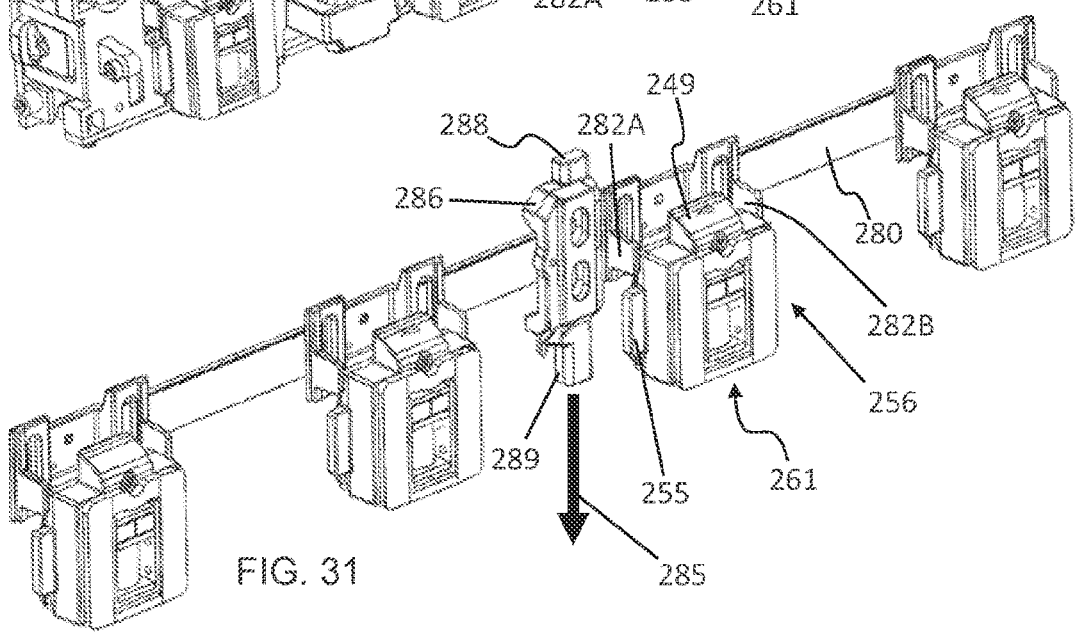
FIG. 31 illustrates a perspective view of a drawer lock assembly, according to an example configuration of the present disclosure.

In some example configurations, the manual release bracket 280 can be an elongated flat sheet metal bracket as illustrated in FIGS. 30-31. The manual release bracket 280 can be slidingly engaged with the holding block 260. A slider 286 can be coupled to the manual release bracket 280. The slider 286 can be activated by the user of the workstation 100 to move it in a first direction 285. When the slider 286 is activated, it can also move the manual release bracket 280 in the first direction 285.

The one or more arms 282 can be coupled to the manual release bracket (e.g., the one or more arms 282 can move with the manual release bracket 280 in the first direction 285). The one or more arms 282 can be configured to contact with the latch arms 255 and 256 when the slider 286 is activated to push the latch 250 towards the solenoid body (e.g., away from the lock tab 248) to manually unlock the drawer 240. A spring (e.g., a torsion spring, extension spring, compressions spring, leaf spring, or the like) can bias the manual release bracket 280 in a second direction opposite the first direction 285 (e.g., the one or more arms can be biased away from the latch arms) when the slider is not activated by the user of the workstation 100. The spring is not shown in FIGS. 30-31.

The upper end 288 of the slider 286 of the first drawer housing 160A (e.g., the drawer housing 160 that is coupled to the computer storage compartment 132 directly) can extend into the interior space of the computer storage compartment 132. User of the workstation 100 can access the upper end 288 of the slider 286 by unlocking the computer storage compartment 132.

In some example configurations where two or more drawer housings are coupled together (e.g., 160A and 160B as illustrated in FIG. 19), the slider of the first drawer housing 160A and the slider of the second drawer housing 160B can be in contact. The upper end of the slider of the second drawer housing 160B can be in contact with the lower end of the slider of the first drawer housing 160A.

When the drawer assembly of FIG. 19 is coupled to the workstation 100, the upper end 288 of the slider 286 of the first drawer housing 160A can extend into the interior space of the computer storage compartment 132. When the user of the workstation 100 presses on the slider 286 of the first drawer housing 160A (e.g., press on to the upper end 288 of the slider 286 located inside the computer storage compartment 132), all the drawers can be unlocked in the first drawer housing 160A and the second drawer housing 160B.

As discussed previously, each drawer housing 160 can have a lock assembly 220, and one or more drawers with different size and shape can be inserted into the drawer housing in some example configurations. The one or more drawers can cooperate with the lock assembly to selectively lock and unlock the one or more drawers. It can be useful to detect if the one or more drawers are locked or unlocked (e.g., the latch 250 is in a locked configuration or in an unlocked configuration). If a detected lock status does not match the expected lock status by the controller (e.g., the controller issues a signal to change the lock status but the detected lock status does not change), the controller can determined that the lock has failed, and then, the controller can take additional actions (e.g., attempt to recover from a failure by re-attempting to lock or unlock, or issue a lock status alert to the user of the workstation 100. The lock status can be detected as discussed below according to some example configurations of the current disclosure.

Figure 32:
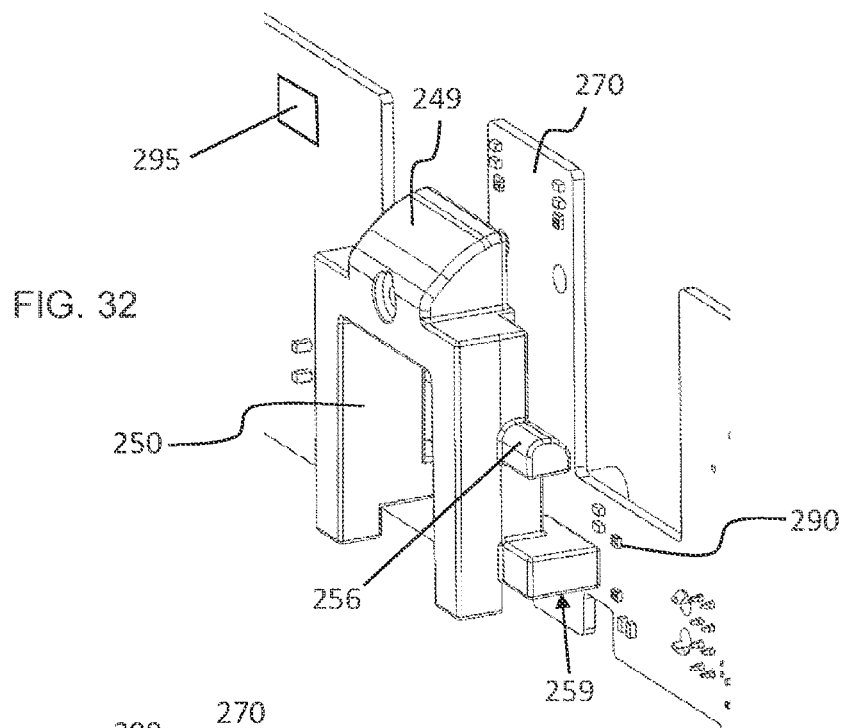
FIG. 32 illustrates a perspective view of the latch and the drawer controller, according to an example configuration of the present disclosure.

FIG. 32 is a perspective view of the latch 250 and the drawer controller 270 according to an example configuration of the current disclosure. The drawer controller 270 can include at least one translation sensor 290. The translation sensor 290 can measure translation of a moveable component (e.g., the latch 250) relative to a reference point (e.g., holding block 260). In some examples, the translation sensor 290 can be coupled to the moveable components (e.g., the latch 250) or to the holding block 260.

A sensor operator 259 (as shown in FIG. 25) can be coupled to (or included in) the latch 250. The translation sensor 290 can detect the sensor operator 259, and the translation sensor 290 can determine the location of (or the change in location of) the sensor operator 259 relative to the sensor 290 (e.g., the sensor 290 can detect the translation of the latch 250). For instance, the translation sensor 290 can include a hall effect sensor, and the sensor operator 259 can include a magnet. The sensor 290 can detect a change in a magnetic field, for instance when the latch 250 is translated. The sensor 290 can modulate an electrical property (e.g., voltage, current, impedance, or the like) when the sensor operator 259 translates relative to the sensor 290. Accordingly, the sensor 290 can measure the translation of the latch 250 relative to the holding block 260. In some example configurations, the sensor 290 can be aligned with the sensor operator 259 when the latch is in the locked configuration.

The sensor 290 (and the sensor operator 259) can include (but is not limited to) one or more of an optical sensor, a potentiometer, an accelerometer, a hall effect sensor, an accelerometer, a proximity sensor, a pressure sensor, a temperature sensor, an IR sensor, a motion detector, a force sensor, a contact sensor, and a current sensor. The drawer controller 270 can include a microcontroller 295. The sensor 290 can be in communication with the microcontroller 295 and the sensor operator 259 can be in communication with the microcontroller 295. Accordingly, the microcontroller 295 can determine the location of the latch 250 with respect to the holding block 260 (shown in FIG. 23) by communicating with the translation sensor 290 that measures the translation of the latch 250. Based on the sensor data received form the sensor 290, the microcontroller 295 can determine whether the latch 250 is in the locked configuration or in the unlocked configuration.

Returning to FIG. 23, the lock assembly 220 includes one or more solenoids. The one or more latches 250 can be coupled to the one or more solenoids. The user of the workstation 100 can activate the one or more solenoids to move the one or more latches 250 between the locked configuration and the unlocked configuration. The one or more solenoids and the drawer controller 270 require electrical energy to operate. In cases when the electrical energy is not available to operate the one or more solenoids, the lock assembly 220 can still be operated by using a manual override system. The manual override system can include a manual release bracket 280 to move the one or more latches 250 between the locked configuration and the unlocked configuration as previously discussed.

When the manual override system is activated, it can disable the operation of the one or more solenoids as discussed earlier in this disclosure. When the power is restored to the workstation 100 after the manual override system is activated, the electronic locking mechanism (e.g., using the one or more solenoids) cannot work until the manual override is removed by the user of the workstation 100. Therefore, it is desirable for the drawer controller (e.g., microcontroller) to know whether the manual override is still active so that microcontroller can issue a status alert to the user to deactivate the manual override. The manual override status can be detected as discussed below according to some example configurations of the current disclosure.

Figure 33:
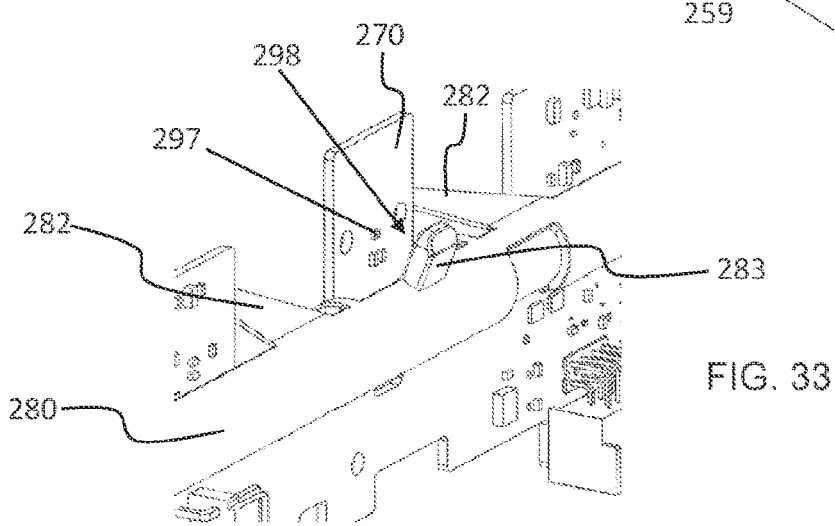
FIG. 33 illustrates a perspective view of the manual release bracket and the drawer controller, according to an example configuration of the present disclosure.

FIG. 33 is a perspective view of the manual release bracket 280 and the drawer controller 270 according to an example configuration of the current disclosure. The drawer controller 270 can include at least one translation sensor 297. The translation sensor 297 can measure translation of a moveable component (e.g., the manual release bracket 280) relative to the translation sensor 297. In some examples, the translation sensor 297 can be coupled to a moveable component (e.g., the manual release bracket 280) or to the holding block 260.

Figure 34:
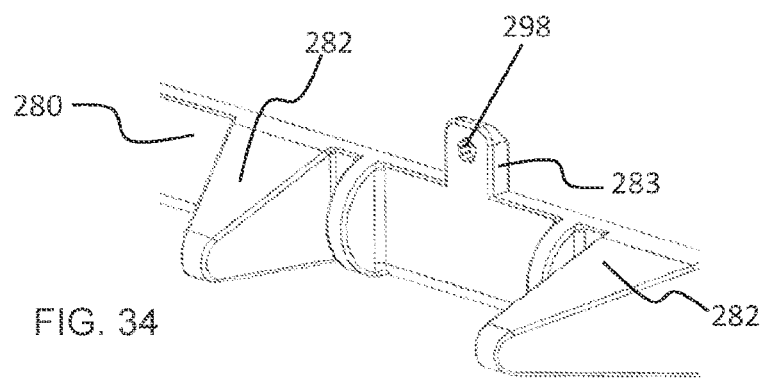
FIG. 34 illustrates a partial perspective view of the manual release bracket of FIG. 33, according to an example configuration of the present disclosure.
Figure 35:
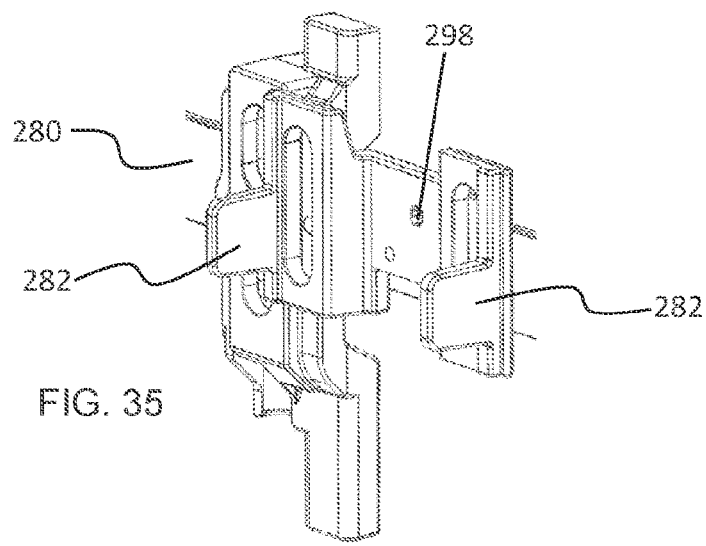
FIG. 35 illustrates a partial perspective view of a manual release bracket, according to an example configuration of the present disclosure.

A sensor operator 298 can be coupled to (or included in) the manual release bracket 280. In some sample configurations, the manual release bracket 280 can have a protrusion 283 as illustrated in FIGS. 33-34. The protrusion 283 can extend from the body of the manual release bracket 280. The sensor operator 298 can be coupled to the protrusion 283. In other example configurations, the sensor operator 298 can be integrated into the body of the manual release bracket 280 as illustrated in FIG. 35. As the manual release bracket 280 move (e.g., translate, rotate, or the like) to activate the manual override, the sensor operator 298 can approach to the translation sensor 297 and it can be detected by the translation sensor 297.

The translation sensor 297 can detect the sensor operator 298, and the translation sensor 297 can determine the location of (or the change in location of) the sensor operator 298 relative to the sensor 297 (e.g., the sensor 297 can detect the translation of the manual release bracket 280). For instance, the translation sensor 297 can include a hall effect sensor, and the sensor operator 298 can include a magnet. The sensor 297 can detect a change in a magnetic field, for instance when the manual release bracket 280 is translated. The sensor 297 can modulate an electrical property (e.g., voltage, current, impedance, or the like) when the sensor operator 298 translates relative to the sensor 297. Accordingly, the sensor 297 can measure the translation of the manual release bracket 280 relative to the holding block 260. In some example configurations, the sensor 297 can be aligned with the sensor operator 298 when the manual override is activated.

The sensor 297 (and the sensor operator 298) can include (but is not limited to) one or more of an optical sensor, a potentiometer, an accelerometer, a hall effect sensor, an accelerometer, a proximity sensor, a pressure sensor, a temperature sensor, an IR sensor, a motion detector, a force sensor, a contact sensor, and a current sensor. The drawer controller 270 can include a microcontroller 295. The sensor 297 can be in communication with the microcontroller 295 and the sensor operator 298 can be in communication with the microcontroller 295. Accordingly, the microcontroller 295 can determine the translation of the manual release bracket 280 by communicating with the translation sensor 297 that measures the translation of the manual release bracket 280. Based on the sensor data received form the sensor 297, the microcontroller 295 can determine whether the manual override is activated.

One or more drawers can be inserted into drawer housing 160 depending on the size of the drawers and the desired configuration. For example, four single-stall drawers 240 can be inserted in the drawer housing 160 as shown in FIG. 21 according to an example configuration of the current disclosure. Each single-stall drawer 240 can have a lock tab 248 coupled to their rear surface 247. Each lock tab 248 can engage with a latch 250 of the lock assembly 220 to secure them inside the drawer housing 160.

Figure 36:
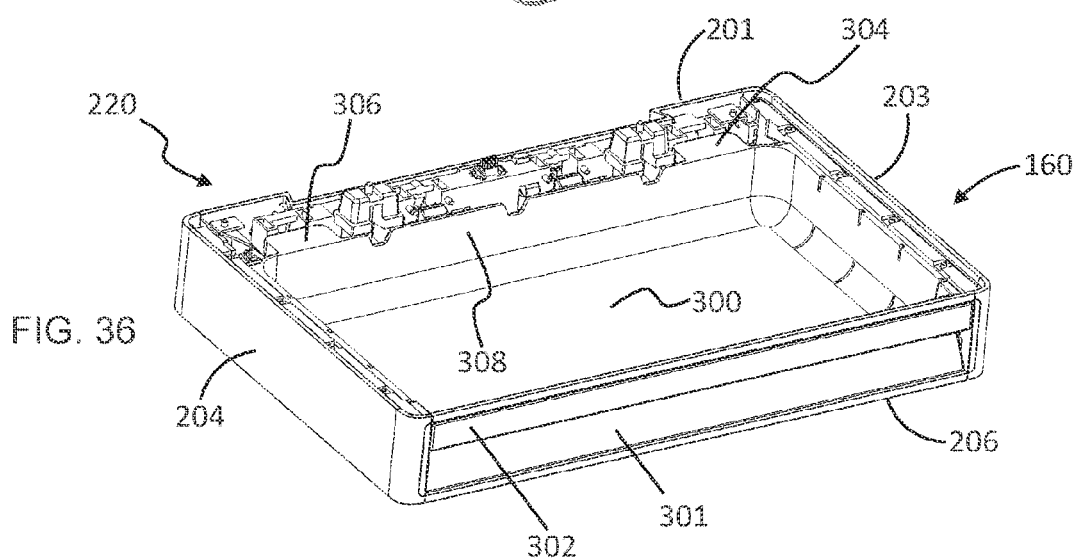
FIG. 36 illustrates a perspective view of a quad-stall drawer as inserted into the drawer housing, according to an example configuration of the present disclosure.
Figure 37:
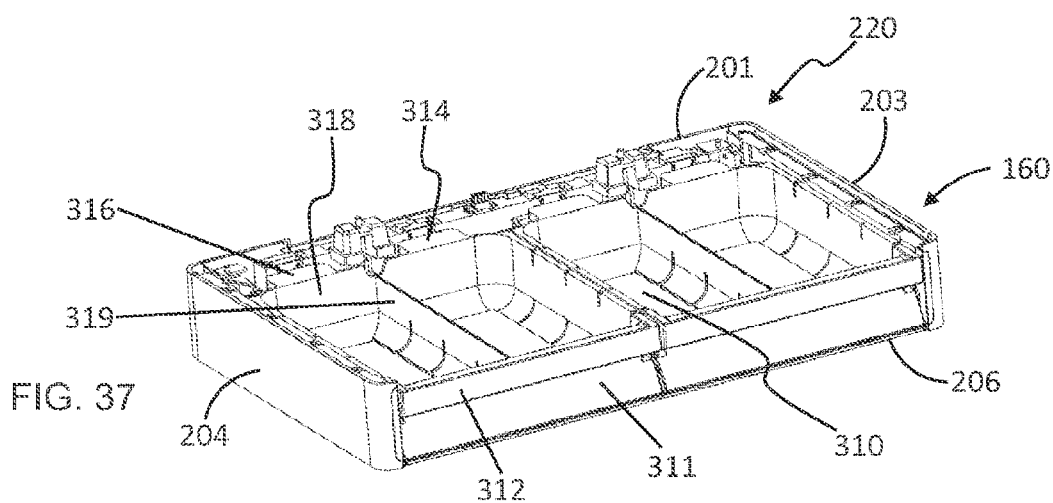
FIG. 37 illustrates a perspective view of two dual-stall drawers as inserted into the drawer housing, according to an example configuration of the present disclosure.

FIGS. 36-37 are perspective views of the drawer housing 160 with different drawer configurations. The upper surface 205 of the drawer housing 160 is removed to show the drawers and the lock assembly 220. Each drawer can be inserted into the drawer housing through the front end 200 of the drawer housing 160, and they can engage with the lock assembly 220 when they are fully inserted into the drawer housing 160.

A quad-stall drawer 300 (e.g., large, four-times as large as a single-stall 240, or the like) can be inserted into the drawer housing 160 as shown in FIG. 36. The quad-stall drawer can have a front surface 301 and a rear surface 308. One or more lock tabs (e.g., a first lock tab 304 and a second lock tab 306) can be coupled to the rear surface 308, and a handle 302 can be coupled to the front surface 301. The one or more lock tabs (e.g., 304 and 306) can engage with the one or more latches 250 of the lock assembly 220 when the quad-stall drawer 300 is fully inserted into the drawer housing 160 to secure it inside the drawer housing 160.

A dual-stall drawer 310 (e.g., mid-size, two-times as large as a single-stall drawer 240, or the like) can be inserted into the drawer housing 160 as shown in FIG. 37. The dual-stall drawer 310 can have a front surface 311 and a rear surface 318. One or more lock tabs (e.g., a first lock tab 314 and a second lock tab 316) can be coupled to the rear surface 318, and a handle 312 can be coupled to the front surface 311. The one or more lock tabs (e.g., 314 and 316) can engage with the one or more latches 250 of the lock assembly 220 when the dual-stall drawer 310 is fully inserted into the drawer housing 160 to secure it inside the drawer housing 160.

FIGS. 38-41 illustrate two drawer housings 160A and 160B coupled to each other according to some example configurations of the current disclosure. The second drawer housing 160B can be located below the first drawer housing 160A. The second drawer housing 160B can be coupled to the first drawer housing 160A via the first 222 and the second 224 mechanical connectors of the second drawer housing 160B. The second drawer housing 160B can also be electrically coupled to the first drawer housing 160A via the electrical connector 226 of the second drawer housing 160B.

Assembly of two drawers illustrated in FIGS. 38-41, can be coupled to the workstation 100 via the first 222 and the second 224 mechanical connectors of the first drawer housing 160A. Similarly, the assembly of two drawers, can be electrically coupled to the workstation 100 via the electrical connector 226 of the first drawer housing 160A.

Drawers (e.g., single, dual, or quad stall drawers) can have dividers to divide the internal space of the drawers. Dividers can be in longitudinal direction (e.g., the divider 319 of quad-stall drawer of FIG. 37), or in lateral direction (e.g., the divider 241 of the single-stall drawer of FIG. 22).

Figure 38:
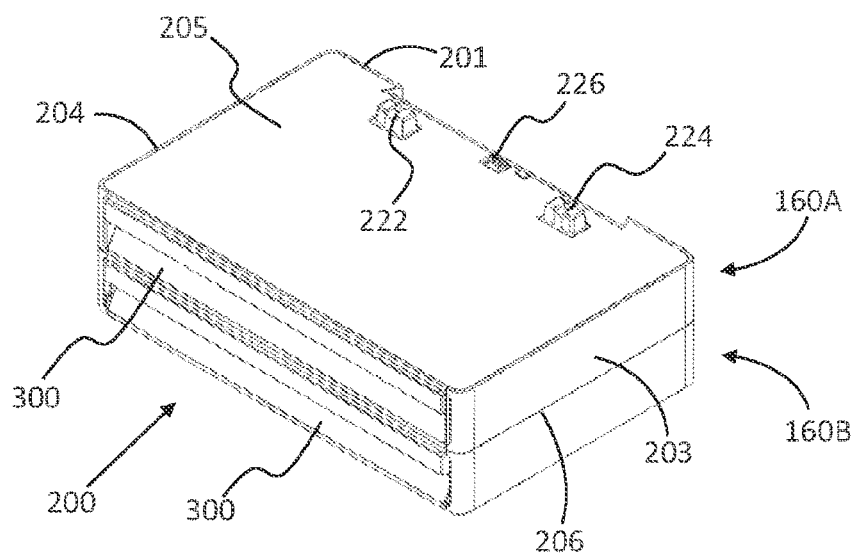
FIG. 38 illustrates two drawer housings coupled in stacked configuration, according to an example configuration of the present disclosure.
Figure 39:
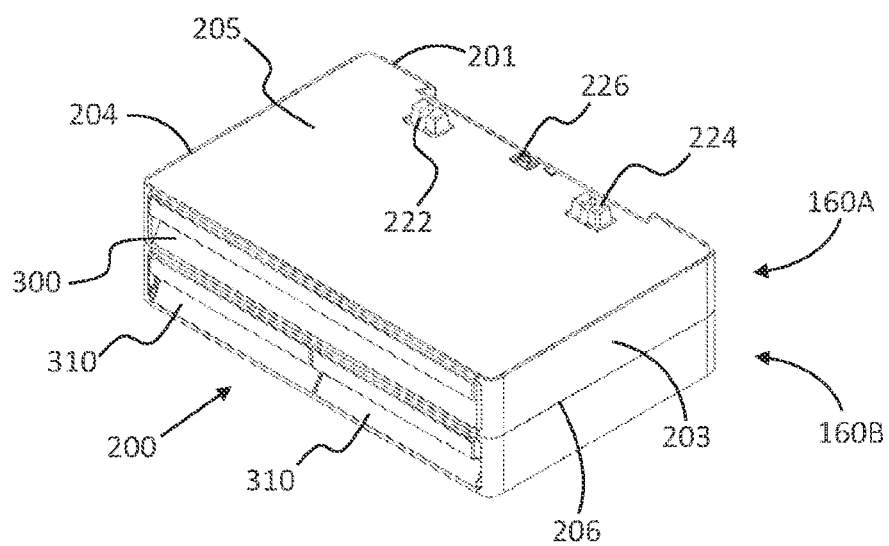
FIG. 39 illustrates two drawer housings coupled in stacked configuration, according to an example configuration of the present disclosure.
Figure 40:
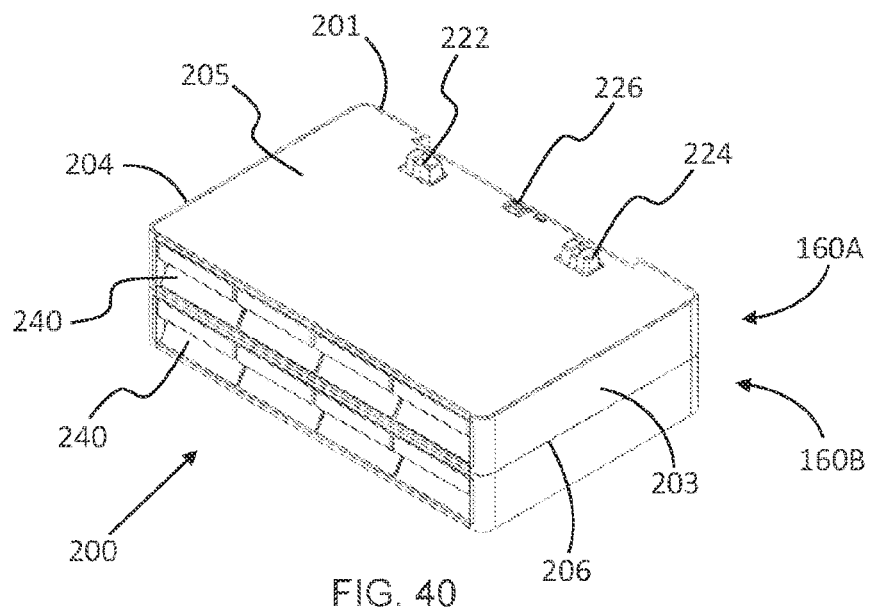
FIG. 40 illustrates two drawer housings coupled in stacked configuration, according to an example configuration of the present disclosure.
Figure 41:
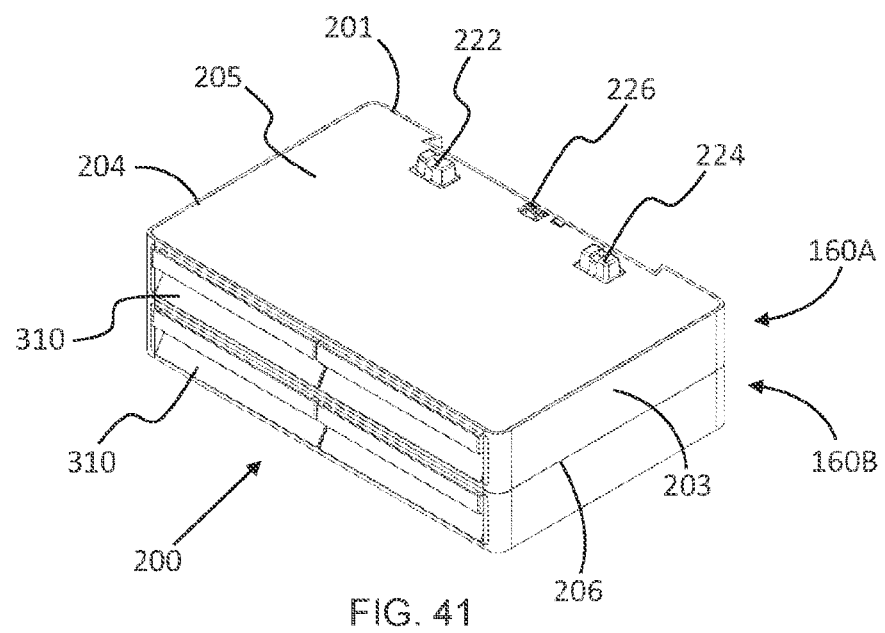
FIG. 41 illustrates two drawer housings coupled in stacked configuration, according to an example configuration of the present disclosure.

In some example configurations, any combination of drawers (e.g., up to four single-stall drawers 240 as illustrated in FIGS. 21 and 40, or up to two dual-stall drawers as illustrated in FIGS. 37 and 41, or a single quad-stall drawer as illustrated in FIGS. 36 and 38, or other combinations of drawers) can be inserted into the drawer housing. In some example configurations where multiple drawer housing are coupled to the workstation 100, the first drawer housing 160A and the second drawer housing 160B can have different combination of drawers as illustrated in FIG. 39.

In some example configurations, operation of drawers included in the one or more drawer housings coupled to the workstation 100 of FIG. 1B can be controlled according to a dynamic drawer addressing method.

FIG. 42 is a block diagram representation of the dynamic drawer addressing method 400. The dynamic drawer addressing method 400 can include a central control unit 125 and the one or more drawer housings 160. The central control unit 125 can be located on the workstation 100 and it can interface with all drawer housings coupled to the workstation 100 via a shared bidirectional data bus 410-411. The central control unit 125 can also directly communicate with the first drawer housing 160A via a first data bus enable signal 420. The first drawer housing 160A can include a second data bus enable signal 430 that can be directly coupled to the second drawer housing 160B. The second data bus enable signal 430 can only communicate with the second drawer housing 160B that can be directly below the first drawer housing 160A. This connection method can be cascaded down to the $N^{th}$ drawer housing 160N.

Each drawer housing (e.g., the first drawing housing 160A, the second drawing housing 160B, and the like) can include a drawer controller 270 and the one or more latches 250. The drawer controller 270 can be coupled to the one or more latches 250 included in the drawer housing 160 to control up to n-number of electromechanical latches (e.g., the first latch 250A, the second latch 250B, and others) to unlock and lock up n-number of individual drawers. The drawer controller 270 can include a processor 273 and a memory 275. At initialization or power on of the workstation 100, the memory 275 in each drawer controller 270 can be preprogrammed with a default address such that each drawer housing 160 can be identical.

The central control unit 125 assigns each drawer housing 160 its own unique address over the shared data bus 410-411. At power on or during initialization, all data bus enable signals (e.g., the first data bus enable signal 420, and the second data bus enable signal 430) can be disabled such that no drawer housing 160 can respond to any communication from the central control unit 125. The central control unit 125 can enable communication to the first drawer housing by enabling the first data bus enable signal 420 that it shares with the first drawer housing 160A only.

Subsequently, using the default preprogrammed address, the central control unit 125 can communicate over the shared data bus 410-411 to send a first unique address to a drawer housing. Since only the first drawer housing 160A has its communication bus 420 enabled or listening, it can receive the first unique address through the shared data bus 410-411 and respond with a confirmation message through the communication bus 420. The central control unit 125 can instruct the first drawer housing 160A that has the first unique address to enable the second data bus enable signal 430 which it shares with the second drawer housing 160B only.

Subsequently, the central control unit 125 can once again use the default preprogrammed address to communicate over the shared data bus 410-411 to send a second unique address to a drawer housing. Both the first drawer housing 160A and the second drawer housing 160B can have their communication bus enabled or listening, but only the second drawer housing 160B can respond to the default preprogrammed address. Thus, the second drawer housing 160B can receive the second unique address through the shared data bus 410-411 and respond with a confirmation message through the communication bus 430.

This described sequence can continue for each respective drawer housings until a confirmation message can no longer be received after an attempt to send the $N^{th}$ unique drawer address. At this point, the central control unit 125 can determine that there can be N−1 drawer housings and that the dynamic addressing has been completed.

Various modular components (e.g., drawer housings, drawers, printers, scanners, computers, or the like) can be added to the workstation 100 during its use. These modules can have various configurations (e.g., drawer configurations, or the like). It is desirable for the central control unit 125 to identify these added modules and their configurations so that the central control unit 125 can monitor the use of these modules and report to the user or issue alerts.

The workstation 100 can have various sensors (e.g., hall effect sensors, optical sensors, or the like) according to some example configurations of the current disclosure. Sensors can be coupled to the central control unit 125. Modules (e.g., drawers) can have sensor operators (e.g., magnets, color coded tape, or the like) embedded in them. Sensor operators can be strategically located on modules so that they can align with sensors when modules are coupled to the workstation 100. Sensors can determine the status of sensor operators during the use of the workstation 100 and communicate their status to the central control unit 125.

An example of a module that can be frequently coupled to the workstation 100 of FIG. 1B is a drawer housing 160 with varying drawer configurations (e.g., single-stall, dual-stall, quad-stall, dual-stall/tall, quad-stall/tall, or the like). Drawer configurations inside a drawer housing 160 can have various features (e.g., size, shape, color, orientation, or the like). The user of the workstation 100 can have flexibility to rearrange the drawer configuration depending on the tasks to be performed using the workstation 100.

In some example implementations, it can be desirable for the central control unit 125 to determine the drawer configuration when the drawer housing 160 is coupled to the workstation 100 and coupled to the central control unit 125. Once the drawer configuration is determined, the central control unit 125 can monitor the use of drawers and report on the status of drawers (e.g., open/closed, present/not-present, locked/unlocked, or the like) and issue alerts to the user of the workstation 100.

The central control unit 125 can learn the drawer configuration either automatically when the drawers are coupled to the workstation 100, or the drawer configuration can be entered by the user of the workstation 100. To prevent mistakes and reduce the amount of data entry by the user of the workstation 100, it is desirable for the central control unit 125 to determine the drawer configuration automatically when the drawers are coupled to the workstation 100. One or more methods explained in this disclosure can be used to determine the drawer configuration automatically.

FIGS. 43A-E are block diagram representations of some example drawer configurations including single-stall 240, dual-stall 310, dual-stall/tall 315, quad-stall 300, and quad-stall/tall drawers 305. Other drawer configurations can also be designed and used within the scope of this disclosure. Any method explained in this disclosure can be applicable to any other drawer configurations as well without limitation. One or more sensor operators (e.g., magnets 500) can be embedded into the drawers as illustrated in FIGS. 43A-E. In some sample configurations, the single-stall drawer 240 can have one sensor operator (e.g., magnet 500A) whereas the dual-stall drawer 310 and the quad-stall drawer 300 can have two sensor operators (e.g., magnets 500A and 500B), and the quad-stall/tall drawer 305 can have four sensor operators (e.g., magnets 500A, 500B, 500C and 500D). Other sensor operator configurations are also considered within the scope of this disclosure. The sensor operators (e.g., magnets) can be strategically located on the drawers to align with one or more sensors (e.g., hall effect sensors located on the drawer controller 270) to identify the specific drawer configuration.

FIGS. 44A-H are block diagram representations of various drawer configurations and the drawer controller 270 according to some example configurations of the current disclosure. The drawer controller 270 can have one or more sensors 600 (e.g., eight sensors 600A, 600B, 600C, 600D, 600E, 600F, 600G, and 600H), and the drawer controller can be separated into one or more regions 610 (e.g., four regions 610A, 610B, 610C, and 610D). Each region 610 can include the one or more sensors 600 (e.g., the first sensor 600A proximate the left end of the region 610A and the second sensor 600B proximate the right end of the region 610A, so on). The microcontroller 295 (shown in FIG. 32) located on the drawer controller 270 can be in communication with all the sensors located on the drawer controller 270.

Figure 45A:
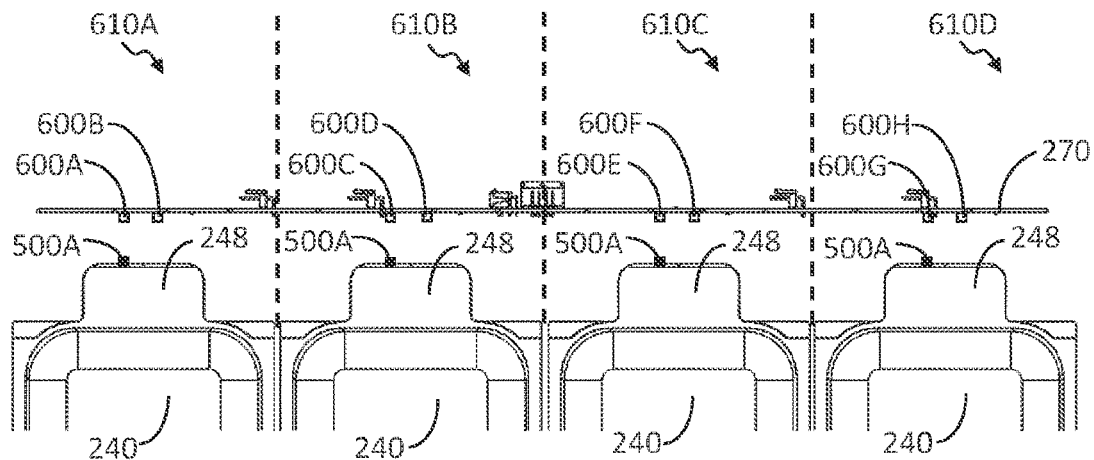
FIG. 45A illustrates a top view of drawer controller and four single-stall drawers, and alignment between sensors and magnets, according to an example configuration of the present disclosure.
Figure 45B:
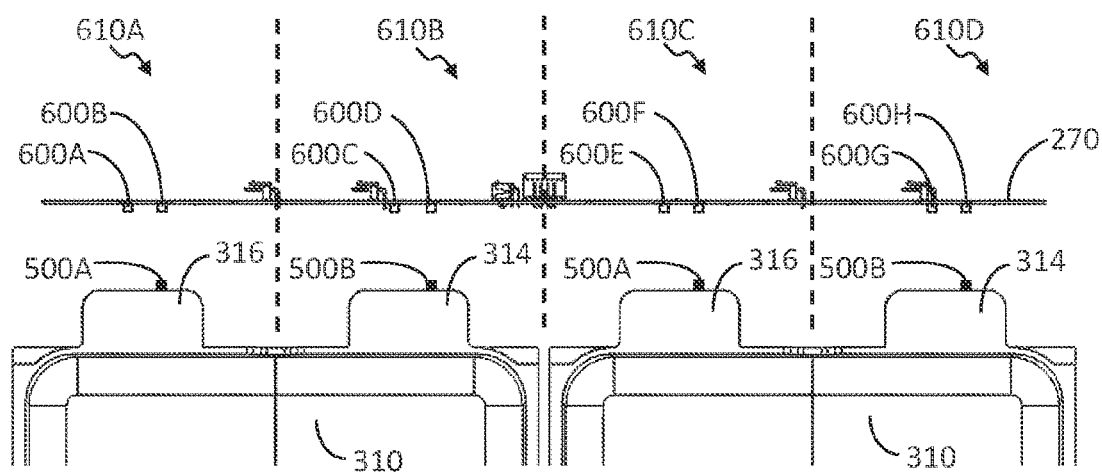
FIG. 45B illustrates a top view of drawer controller and two dual-stall drawers, and alignment between sensors and magnets, according to an example configuration of the present disclosure.
Figure 45C:
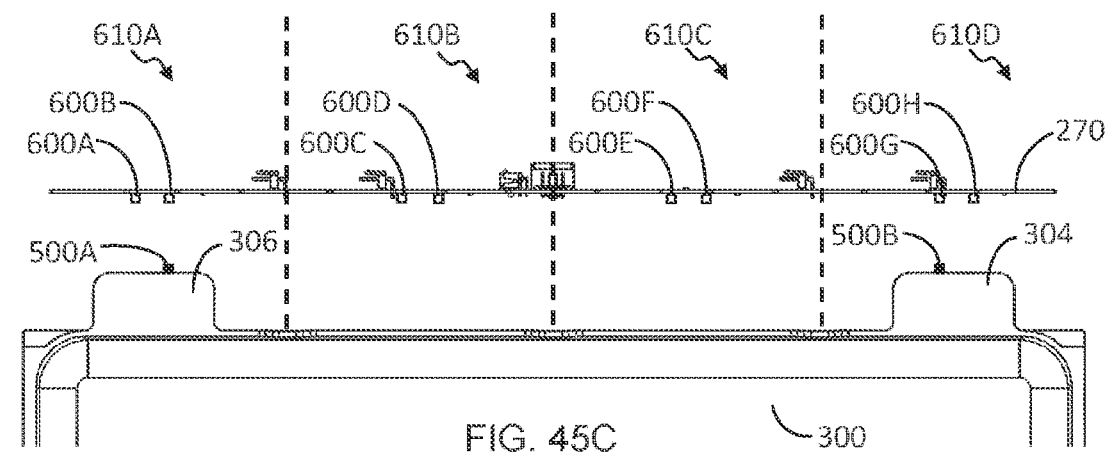
FIG. 45C illustrates a top view of drawer controller and a quad-stall drawer, and alignment between sensors and magnets, according to an example configuration of the present disclosure.

FIGS. 45A-C is a top view of the rear end of the drawers against the drawer controller 270 according to some example configurations of the current disclosure. Depending on its size, each drawer can overlap with the one or more regions 610 of the drawer controller 270. For example, in FIG. 45A a single-stall drawer 240 can overlap with a single region 610A whereas in FIG. 45B a dual-stall drawer 310 can overlap with two regions 610A-B, and in FIG. 45C a quad-stall drawer 300 can overlap with four regions 610A-B-C-D).

As shown in FIGS. 45A-C, the sensor operators 500 can be coupled to the rear end of the lock tabs (e.g., lock tab 248 of a single-stall drawer 240, so on) facing the drawer controller 270. The sensor operators 500 (e.g., magnets) can be located on each drawer to align with sensors 600 located in the one or more regions 610 of the drawer controller 270. Each different drawer configuration can have a unique arrangement of sensor operator locations (e.g., magnet locations). Depending on the alignment between the one or more sensors 600 with the one or more sensor operators 500, the specific drawer configuration and its location within the drawer housing 160 can be automatically detected by the central control unit 125 of the workstation 100.

Figure 46:
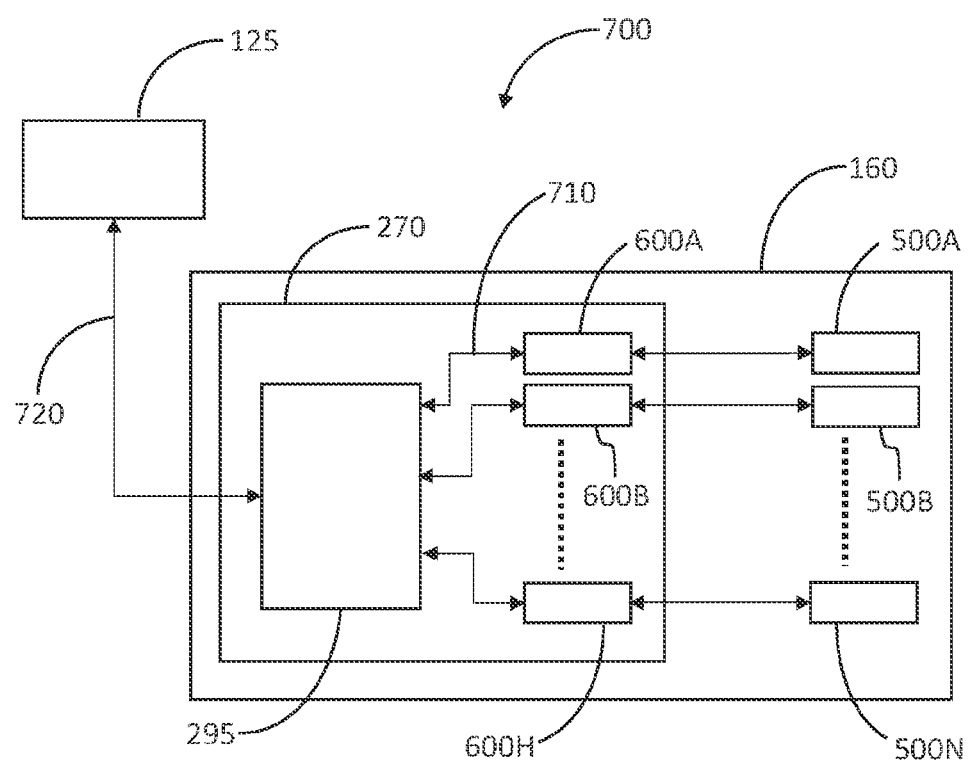
FIG. 46 illustrates a block diagram of drawer detection system, according to an example configuration of the present disclosure.

FIG. 46 is a block diagram representation of the module (e.g., drawer) detection system 700. Each unit 160 (e.g., the drawer housing) can include a controller 270 (e.g., the drawer controller). The controller 270 can include a microcontroller 295 and the one or more sensors 600 (e.g., 600A-thru-H). The one or more sensors 600 can communicate with the microcontroller 295 (e.g., through a signal line 710). The one or more sensor operators 500 (e.g., 500A-thru-N) can be coupled to modular components (e.g., drawers). N-number of sensor operators (e.g., N can be any integer number) can be coupled to the modular components depending on their configuration (e.g., size, shape, orientation, or the like). When sensor operators 500 are located in close proximity of the controller 270 (e.g., drawers can be inserted into the drawer housing), the one or more sensor operators 500 can be detected by the one or more sensors 600. Depending on the match between the sensors 600 and sensor operators 500, the microcontroller 295 of the controller 270 can determine the configuration of the module (e.g., can determine the size and location of the drawer) and communicate it to the central control unit 125 via the communication line 720.

Figure 44A:
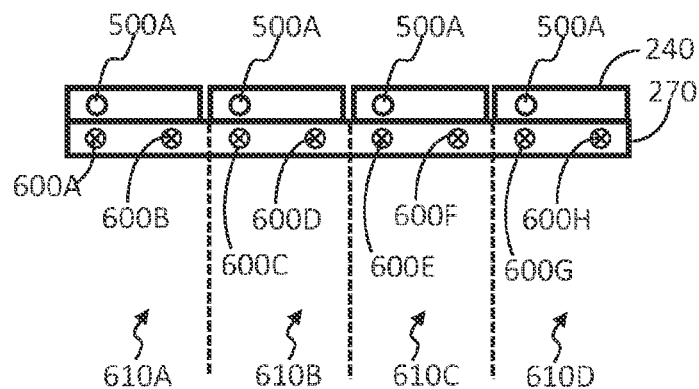
FIG. 44A illustrates a block diagram representing the overlap between drawer controller and four single-stall drawers, according to an example configuration of the present disclosure.
Figure 44B:
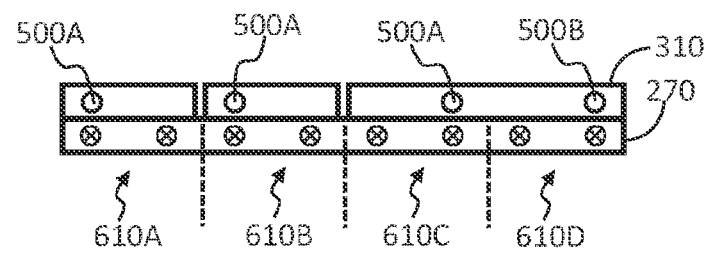
FIG. 44B illustrates a block diagram representing the overlap between drawer controller and two single-stall, and one dual-stall drawers, according to an example configuration of the present disclosure.
Figure 44C:
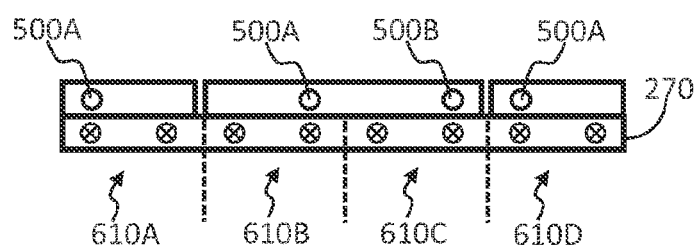
FIG. 44C illustrates a block diagram representing the overlap between drawer controller and two single-stall, and one dual-stall drawers, according to an example configuration of the present disclosure.
Figure 44D:
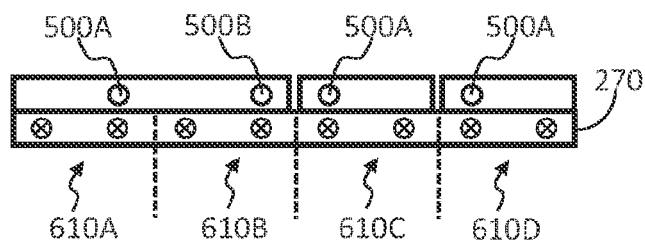
FIG. 44D illustrates a block diagram representing the overlap between drawer controller and two single-stall, and one dual-stall drawers, according to an example configuration of the present disclosure.

In an example configuration, a single-stall drawer 240 can have the sensor operator 500A (e.g. magnet) located proximate the left side of the lock tab 248 as illustrated in FIG. 45A. In an example configuration as illustrated in FIGS. 44A and 45A, a single-stall drawer 240 can overlap with only one region (e.g., 610A, or the like) of the drawer controller 270. When the single-stall drawer 240 is inserted into the drawer housing 160, a sensor can align with a sensor operator (e.g., the sensor 600A can align with the magnet 500A, so on). Since only one sensor operator (e.g., magnet 500A located proximate the left side of the lock tab 248) can be aligned with only one sensor (e.g., sensor 600A located proximate the left side of the region 610A), the central control unit 125 can detect that a single-stall drawer 240 is inserted into the drawer housing 160 to overlap with the region 610A of the drawer controller 270. In another example configuration, if only one sensor operator (e.g., magnet 500A) can be aligned with only one sensor (e.g., sensor 600G), the central control unit 125 can detect that a single-stall drawer 240 is inserted into the drawer housing 160 to overlap with the region 610D of the drawer controller 270. Similarly, in yet other configurations, the single-stall drawer 240 can be inserted into the drawer housing 160 to overlap with other regions 610 of the drawer controller 270, and it can be detected by the central control unit 125.

Figure 44E:
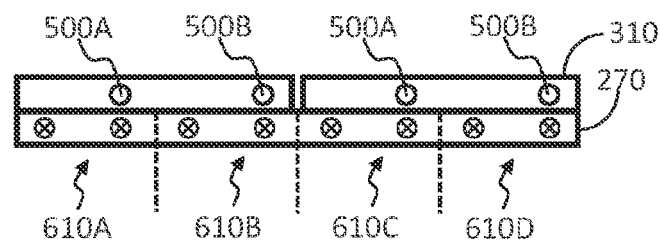
FIG. 44E illustrates a block diagram representing the overlap between drawer controller and two dual-stall drawers, according to an example configuration of the present disclosure.

In another example configuration, a dual-stall drawer 310 can have two lock tabs 314 and 316 as illustrated in FIG. 45B, and a sensor operator can be coupled to each lock tab (e.g., magnet 500A can be coupled to the lock tab 316 proximate to its right side, and magnet 500B can be coupled to the lock tab 314 proximate to its right side). In an example configuration as illustrated in FIGS. 44E and 45B, a dual-stall drawer 310 can overlap with two adjacent regions (e.g., 610A and 610B, so on) of the drawer controller 270. When the dual-stall drawer 310 is inserted into the drawer housing 160, two sensors can align with two sensor operators (e.g., magnet 500A located proximate the right side of the lock tab 316 can align with the sensor 600B located proximate the right side of the region 610A, and magnet 500B located proximate the right side of the lock tab 314 can align with the sensor 600D located proximate the right side of the region 610B), the central control unit 125 can detect that a dual-stall drawer 310 is inserted into the drawer housing 160 to overlap with the regions 610A-B of the control board 270. Similarly, in other configurations, the dual-stall drawer 310 can be inserted into the drawer housing 160 to overlap with two other regions 610 of the drawer controller 270, and it can be detected by the central control unit 125.

Figure 44F:
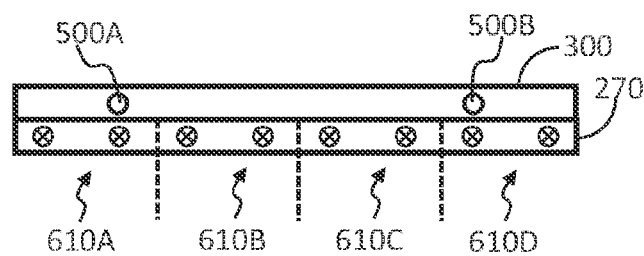
FIG. 44F illustrates a block diagram representing the overlap between drawer controller and one quad-stall drawer, according to an example configuration of the present disclosure.
Figure 44G:
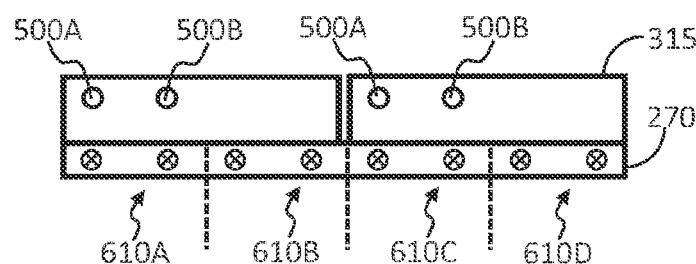
FIG. 44G illustrates a block diagram representing the overlap between drawer controller and two dual-stall/tall drawers, according to an example configuration of the present disclosure.

In yet another example configuration, a quad-stall drawer 300 can have two lock tabs 304 and 306 as illustrated in FIG. 45C, and a sensor operator can be coupled to each lock tab (e.g., magnet 500A can be coupled to the lock tab 306 proximate to its right side, and magnet 500B can be coupled to the lock tab 304 proximate to its left side). In an example configuration as illustrated in FIGS. 44F and 45C, a quad-stall drawer 300 can overlap with four regions (e.g., 610A-B-C-D) of the drawer controller 270. When the quad-stall drawer 300 is inserted into the drawer housing 160, two sensors can align with two sensor operators (e.g., magnet 500A located proximate the right side of the lock tab 306 can align with the sensor 600B located proximate the right side of the region 610A, and magnet 500B located proximate the left side of the lock tab 304 can align with the sensor 600G located proximate the left side of the region 610D), the central control unit 125 can detect that a quad-stall drawer 300 is inserted into the drawer housing to overlap with the regions 610A-D of the drawer controller 270.

Some example configurations of the current disclosure have been discussed above to illustrate methods to detect the configuration and location of various modular components (e.g., drawers) as they are coupled to the workstation 100 of FIG. 1B (e.g., inserted into the drawer housings). The methods discussed can include unique arrangements of sensors (e.g., hall effect sensors located on the drawer controller), and sensor operators (e.g., magnets embedded into the drawers). Some example arrangements of sensors and sensor operators are illustrated above. Other arrangements can also be used and they are considered within the scope of this disclosure.

Figure 44H:
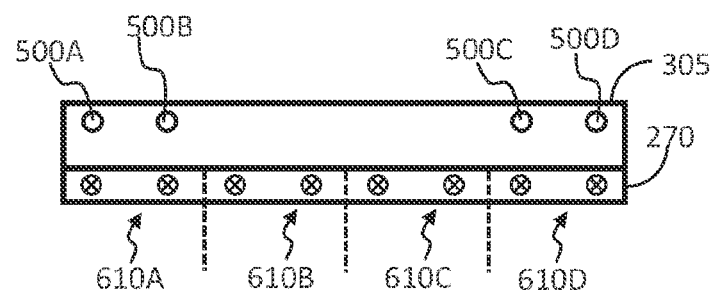
FIG. 44H illustrates a block diagram representing the overlap between drawer controller and one quad-stall/tall drawer, according to an example configuration of the present disclosure.

When a modular component (e.g., a drawer housing 160A, or a drawer 240, or the like) is coupled to the workstation 100, the one or more sensor operators located on the modular components (e.g., magnet 500 located on the drawer 240, or the like) can align with the one or more sensors coupled to the workstation 100 (e.g., hall effect sensor 600 located on the drawer controller 270, or the like), and an electronic device located on the workstation (e.g., a microcontroller 295 located on the drawer controller 270, or the like) can determine which sensors are present and where they are located. Since the arrangement of sensors can be unique to each different configuration or type of the modular component (e.g., a single-stall drawer can have only one sensor operator detected by only one sensor as shown in FIG. 45A, or a quad-stall/tall drawer can have four sensor operators detected by four sensors as shown in FIG. 44H, or the like), the electronic device can then use this knowledge (e.g., by using a software algorithm, look up table, or other method) to determine the type, configuration, and location of the modular component coupled to the workstation 100.

ADDITIONAL NOTES AND ASPECTS

Aspect 1 may include or use subject matter (such as an apparatus, a system, a device, a method, a means for performing acts, or a device readable medium including instructions that, when performed by the device, may cause the device to perform acts), such as may include or use an appliance with changeable components, the appliance comprising: a support structure; a housing coupled to the support structure, wherein the housing is configured to receive at least one component; a plurality of sensor operators coupled to the at least one component; a plurality of sensors coupled to the appliance, wherein the plurality of sensors configured to detect a transfer of the plurality of sensor operators; and a control unit in communication with the plurality of sensors, wherein the control unit is adapted to determine a configuration of the at least one component.

Aspect 2 may include or use, or may optionally be combined with the subject matter of Aspect 1, to optionally further including a worksurface supported by the support structure.

Aspect 3 may include or use, or may optionally be combined with the subject matter of Aspect 1, to optionally include or use wherein the housing is a drawer housing.

Aspect 4 may include or use, or may optionally be combined with the subject matter of Aspect 3, to optionally include or use wherein the component is a drawer.

Aspect 5 may include or use, or may optionally be combined with the subject matter of Aspect 1, to optionally include or use wherein the housing is a storage compartment.

Aspect 6 may include or use, or may optionally be combined with the subject matter of Aspect 5, to optionally include or use wherein the at least one component includes at least one of a computer, a data storage device, a printer, a charger, a data cable, a scanner, or an electronic device.

Aspect 7 may include or use, or may optionally be combined with the subject matter of Aspect 1, to optionally include or use wherein the housing is a battery holding bracket.

Aspect 8 may include or use, or may optionally be combined with the subject matter of Aspect 7, to optionally include or use wherein the at least one component is a battery.

Aspect 9 may include or use, or may optionally be combined with the subject matter of Aspect 1, to optionally include or use wherein the housing is an accessory holding bracket.

Aspect 10 may include or use, or may optionally be combined with the subject matter of Aspect 9, to optionally include or use wherein the component includes at least one of a scanner, a wipes container, a temperature sensor, a thermal camera, or a storage bin.

Aspect 11 may include or use, or may optionally be combined with the subject matter of Aspect 1, to optionally include or use wherein the sensor includes at least one of a hall effect sensor, a potentiometer, an accelerometer, a proximity sensor, a pressure sensor, a temperature sensor, an IR sensor, a motion detector, a force sensor, a contact sensor, a current sensor, or an optical sensor.

Aspect 12 may include or use, or may optionally be combined with the subject matter of Aspect 1, to optionally further comprising: a wheeled base, wherein the support structure is coupled to the wheeled base.

Aspect 13 may include or use, or may optionally be combined with the subject matter of Aspect 1, to optionally further comprising: a movable bracket slidably coupled to the support structure.

Aspect 14 may include or use, or may optionally be combined with the subject matter of Aspect 13, to optionally further comprising: a lift assembly, wherein the lift assembly is coupled between the movable bracket and the support structure, and wherein the lift assembly is configured to translate the housing relative to the support structure.

Aspect 15 may include or use subject matter (such as an apparatus, a system, a device, a method, a means for performing acts, or a device readable medium including instructions that, when performed by the device, may cause the device to perform acts), such as may include or use an appliance with changeable components, the appliance comprising: a support structure; a housing coupled to the support structure, wherein the housing is configured to receive at least one component; a lock assembly having one or more latches, wherein the one or more latches are adapted to engage with the at least one component in a locked configuration and adapted to disengage from the at least one component in an unlocked configuration; a plurality of sensor operators coupled to the one or more latches; a plurality of sensors coupled to the appliance, wherein the plurality of sensors are configured to detect a transfer of the plurality of sensor operators; and a control unit in communication with the plurality of sensors, wherein the control unit is adapted to determine a configuration of one or more latches when the one or more latches are in the locked configuration or in the unlocked configuration.

Aspect 16 may include or use, or may optionally be combined with the subject matter of Aspect 15, to optionally further comprising: a manual release bracket, wherein the manual release bracket is adapted to selectively engage with the one or more latches in an unlocked configuration; a manual release sensor operator coupled to the manual release bracket; a manual release sensor coupled to the appliance, wherein the manual release sensor is configured to detect a transfer of the manual release sensor operator; and a control unit in communication with the manual release sensor, wherein the control unit is adapted to determine a configuration of the manual release bracket when it is in the unlocked configuration.

Aspect 17 may include or use subject matter (such as an apparatus, a system, a device, a method, a means for performing acts, or a device readable medium including instructions that, when performed by the device, may cause the device to perform acts), such as may include or use a workstation including a drawer system, the workstation comprising: a support structure; a worksurface coupled to the support structure; a drawer housing coupled to the support structure, wherein the drawer housing is configured to receive a plurality of drawers; a plurality of sensor operators coupled to the plurality of drawers; a plurality of sensors coupled to the drawer housing, wherein the plurality of sensors are configured to detect a transfer of the plurality of sensor operators; and a control unit in communication with the plurality of sensors and configured to determine a configuration of at least one of the plurality of drawers.

Aspect 18 may include or use, or may optionally be combined with the subject matter of Aspect 17, to optionally include or use wherein the workstation further comprising a wheeled base, wherein the support structure is coupled to the wheeled base.

Aspect 19 may include or use, or may optionally be combined with the subject matter of Aspect 17, to optionally further comprising a movable bracket slidably coupled to the support structure.

Aspect 20 may include or use, or may optionally be combined with the subject matter of Aspect 19, to optionally further comprising: a lift assembly, wherein the lift assembly is coupled between the movable bracket and the support structure, and wherein the lift assembly is configured to translate the drawer housing relative to the support structure.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific examples in which the present subject matter can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or configurations, with each claim standing on its own as a separate example, and it is contemplated that such examples can be combined with each other in various combinations or permutations. The scope of the present subject matter should be determined with reference to the appended claims, along with the full scope of equivalents to which such claims are entitled.

The claimed invention is:

1. A workstation comprising:
   a wheeled base;
   a riser coupled to the wheeled base, the riser including:
      a support column extending from the wheeled base; and
      a movable bracket slidingly coupled to the support column;
   a cabinet coupled to the movable bracket, the movable bracket configured to enable selective translation of the cabinet relative to the riser in a direction toward the wheeled base or in a direction away from the wheeled base; and
   drawer housings including:

a recessed section oriented toward the riser, the recessed section configured to receive at least a portion of the cabinet therein to form a sliding engagement between the drawer housings and the cabinet, the sliding engagement configured to enable selective translation of the drawer housings relative to the cabinet in the direction toward the wheeled base or in the direction away from the wheeled base; and one or more latches slidingly coupled to the drawer housings and operable to secure the drawer housings to the cabinet.

2. The workstation of claim 1, comprising:
a head unit coupled to the movable bracket, the head unit including:
   a worksurface;
   a storage compartment located at least partially below the worksurface;
   a display riser configured to hold a display above the worksurface; and
   a keyboard tray located at least partially below the storage compartment.

3. The workstation of claim 2, comprising:
a lift assembly coupled to the movable bracket and the support column, the lift assembly configured to enable translation of the head unit relative to the riser.

4. The workstation of claim 2, wherein the drawer housings comprise:
   a first drawer housing secured to the head unit; and
   a second drawer housing secured to the first drawer housing.

5. The workstation of claim 4, comprising:
   one or more first fasteners configured to secure the first drawer housing to the head unit; and
   one or more second fasteners configured to secure the second drawer housing to the first drawer housing.

6. The workstation of claim 5, wherein the one or more first fasteners and the one or more second fasteners are oriented in a vertical direction.

7. The workstation of claim 5, wherein the one or more second fasteners are coupled to the one or more first fasteners.

8. The workstation of claim 7, wherein the one or more first fasteners comprises:
   a first stud extending between an upper end and a lower end, the first stud including:
      a first threaded aperture formed in the lower end of the first stud;
   a first holding block;
   a first slider including a first set of keying features to engage with the first holding block and the first stud; and
   a first spring engaged with the first slider to bias the first slider toward the lower end of the first stud to cause the first set of keying features to engage the first holding block and the first stud to limit rotation of the first stud.

9. The workstation of claim 8, wherein the one or more second fasteners comprises:
   a second stud extending between an upper end and a lower end, the second stud including:
      a threaded surface on the upper end complementary to the first threaded aperture of the first stud; and
      a second threaded aperture formed in the lower end of the second stud;
   a second holding block;
   a second slider including a second set of keying features to engage with the second holding block and the second stud; and
   a second spring engaged with the second slider to bias the second slider toward the lower end of the second stud to cause the second set of keying features to engage with the second holding block and the second stud to limit rotation of the second stud.

10. The workstation of claim 9, wherein moving the second slider toward the upper end of the second stud disengages the second set of keying features from the second holding block and the second stud, and wherein when the second set of keying features is disengaged from the second holding block and the second stud, the second stud is rotatable with relation to the first stud to rotate the threaded surface on the upper end of the second stud to engage the threaded surface on the upper end of the second stud and the first threaded aperture of the first stud to secure the second drawer housing to the first drawer housing.

11. The workstation of claim 1, comprising:
   a power station configured to provide power to the workstation.

12. A workstation comprising:
   a wheeled base;
   a riser coupled to the wheeled base, the riser including:
      a support column extending from the wheeled base; and
      a movable bracket slidingly coupled to the support column;
   a cabinet coupled to the movable bracket, the movable bracket configured to enable selective translation of the cabinet relative to the riser in a direction toward the wheeled base or in a direction away from the wheeled base; and
   a drawer housing including:
      a recessed section oriented toward the riser, the recessed section configured to receive at least a portion of the cabinet therein to form a sliding engagement between the drawer housing and the cabinet, the sliding engagement configured to enable selective translation of the drawer housing relative to the cabinet in the direction toward the wheeled base or in the direction away from the wheeled base; and
      one or more latches slidingly coupled to the drawer housing and operable to secure the drawer housing to the cabinet.

13. The workstation of claim 12, comprising:
a head unit coupled to the movable bracket, the head unit including:
   a worksurface;
   a storage compartment located at least partially below the worksurface;
   a display riser configured to hold a display above the worksurface; and
   a keyboard tray located at least partially below the storage compartment.

14. The workstation of claim 13, comprising:
a lift assembly coupled to the movable bracket and the support column, the lift assembly configured to enable translation of the head unit relative to the riser.

15. The workstation of claim 13, wherein the drawer housing comprises:
   a first drawer housing secured to the head unit.

16. The workstation of claim 15, comprising:
   one or more first fasteners configured to secure the first drawer housing to the head unit.

17. The workstation of claim 16, wherein the one or more first fasteners comprises:

a first stud extending between an upper end and a lower end, the first stud including:
  a first threaded aperture formed in the lower end of the first stud;
a first holding block;
a first slider including a first set of keying features to engage with the first holding block and the first stud; and
a first spring engaged with the first slider to bias the first slider toward the lower end of the first stud to cause the first set of keying features to engage the first holding block and the first stud to limit rotation of the first stud.

18. The workstation of claim 17, comprising:
a second drawer housing secured to the first drawer housing; and
one or more second fasteners configured to secure the second drawer housing to the first drawer housing.

19. The workstation of claim 18, wherein the one or more second fasteners comprises:
a second stud extending between an upper end and a lower end, the second stud including:
  a threaded surface on the upper end complementary to the first threaded aperture of the first stud; and
  a second threaded aperture formed in the lower end of the second stud;
a second holding block;
a second slider including a second set of keying features to engage with the second holding block and the second stud; and
a second spring engaged with the second slider to bias the second slider toward the lower end of the second stud to cause the second set of keying features to engage with the second holding block and the second stud to limit rotation of the second stud.

20. The workstation of claim 19, wherein moving the second slider toward the upper end of the second stud disengages the second set of keying features from the second holding block and the second stud, and wherein when the second set of keying features is disengaged from the second holding block and the second stud, the second stud is rotatable with relation to the first stud to rotate the threaded surface on the upper end of the second stud to engage the threaded surface on the upper end of the second stud and the first threaded aperture of the first stud to secure the second drawer housing to the first drawer housing.

* * * * *